(12) United States Patent
He et al.

(10) Patent No.: US 8,450,062 B2
(45) Date of Patent: May 28, 2013

(54) SOCS-3 PROMOTER METHYLATION IN CANCER

(75) Inventors: Biao He, San Mateo, CA (US); Liang You, San Francisco, CA (US); Zhidong Xu, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 124 days.

(21) Appl. No.: 12/701,432

(22) Filed: Feb. 5, 2010

(65) Prior Publication Data

US 2010/0292162 A1  Nov. 18, 2010

Related U.S. Application Data

(63) Continuation of application No. 10/570,916, filed as application No. PCT/US2004/029037 on Sep. 3, 2004, now abandoned.

(60) Provisional application No. 60/500,659, filed on Sep. 5, 2003.

(51) Int. Cl.
   *C12Q 1/68* (2006.01)
   *C12Q 1/00* (2006.01)

(52) U.S. Cl.
   USPC .............. 435/6.11; 435/4; 435/6.1; 435/6.14

(58) Field of Classification Search
   USPC .................................. 435/4, 6.1, 6.11, 7.23
   See application file for complete search history.

(56) References Cited

FOREIGN PATENT DOCUMENTS

WO    WO 2004/022778 A1    3/2004

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No. 850).*
Kaiser (Science, 2006, 313: 1370).*
Bowie, James U. et al., "Deciphering the Message in Protein Sequences: Tolerance to Amino Acid Substitutions", *Science*, vol. 247, pp. 1306-1310 (1990).
Burgess, Wilson H. et al., "Activities of Heparin-binding (Acidic Fibroblast) Growth Factor-1 from Its Receptor-binding Activities by Site-directed Mutagenesis of a Single Lysine Residue", *The Journal of Cell Biology*, vol. 111, pp. 2129-2138 (1990).
Dong, Jin-Tang et al., "Deletion at 13q21 Is Associated with Aggressive Prostate Cancers", *Cancer Research*, vol. 60, pp. 3880-3883 (2000).
He, Biao et al., "SOCS-3 is frequently silenced by hypermethylation and suppresses cell growth in human lung cancer", *PNAS*, vol. 100., No. 24, pp. 14133-14138 (2003).
He, Biao et al., "Cloning and characterization of a functional promoter of the human SOCS-3 gene", *Biochemical and Biophysical Research Communications*, vol. 301, pp. 386-391 (2003).
Kibel, Adam S. et al., "Loss of Heterozygosity at 12p12-13 in Primary and Metastic Prostate Adenocarcinoma", *The Journal of Urology*, vol. 164, pp. 192-196 (2000).
Lazar, Elaine et al., "Transforming Growth Factor ∞: Mutation of Aspartic Acid 47 and Leucine 48 Results in Different Biological Activities", *Molecular and Cellular Biology*, vol. 8, No. 3, pp. 1247-1252 (1988).
Russo, Vincenzo et al., "Expression of the Mage Gene Family in Primary and Metastatic Human Breast Cancer: Implications for Tumor Antigen-Specific Immunotherapy", *Int. J. Cancer (Pred. Oncol.)*, vol. 64, pp. 216-221 (1995).
Wilkman, Harriet et al., "Identification of differentially expressed genes in pulmonary adenocarcinoma by using cDNA array", *Oncogene*, vol. 21, pp. 5804-5813 (2002).

* cited by examiner

*Primary Examiner* — Stephen Rawlings
*Assistant Examiner* — Yan Xiao
(74) *Attorney, Agent, or Firm* — Morrison & Foerster LLP

(57) ABSTRACT

This invention provides compositions and methods for the diagnosis and treatment of cancers that exhibit decreased SOCS-3 expression.

4 Claims, 10 Drawing Sheets

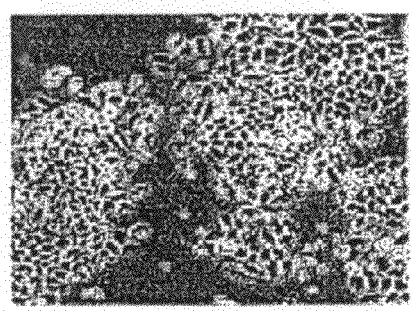
FIG. 5a
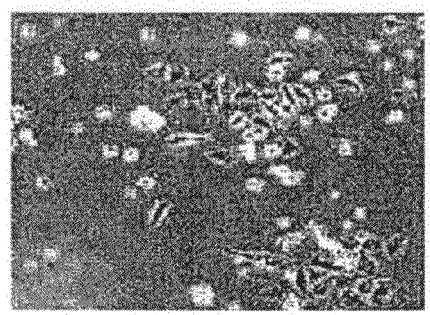
FIG. 5b
FIG. 5c
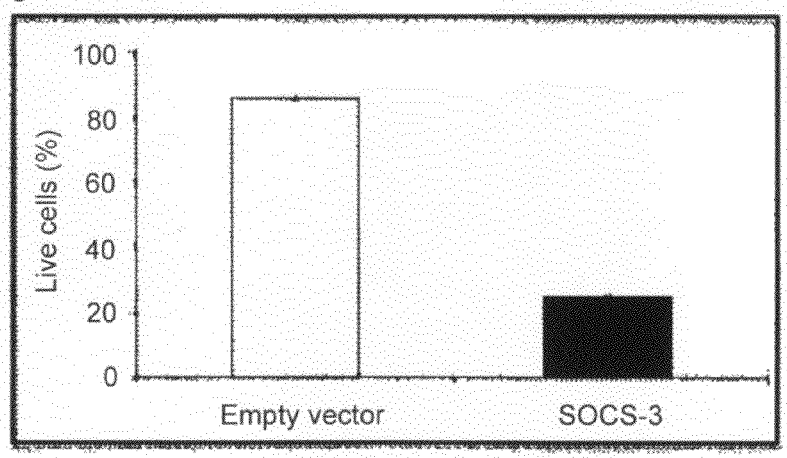
FIG. 5d
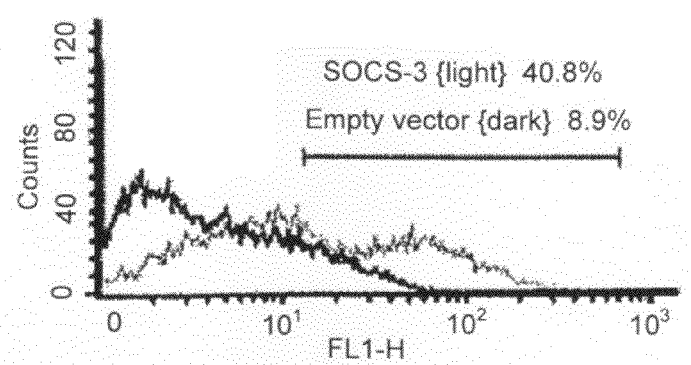

| Case 1 | Case 2 | Case 3 | Case 4 | Case 5 | Case 6 |
|---|---|---|---|---|---|
| T | T | T | T | T | T |
| U   M | U   M | U   M | U   M | U   M | U   M |

*FIG. 7*

SOCS-3 PROMOTER METHYLATION IN CANCER

CROSS-REFERENCE TO RELATED APPLICATIONS

This application claims the benefit of U.S. provisional application No. 60/500,659, filed Sep. 5, 2003, which application is herein incorporated by reference.

BACKGROUND OF THE INVENTION

The Janus kinase (JAK)/signal transducers and activators of transcription (STAT) signaling play important roles in a number of important biologic responses, including immune function, cellular growth, differentiation, and hematopoieses (Cooney, *Shock* 17:83-90, 2002).

It has been reported that abnormalities of the JAK/STAT pathway are associated with cancer (Garcia, et al., *Cell Growth Differ.* 8:1267-1276, 1997; Ihle *Nature* 377:591-594, 1995; Boudny & Kovarik *Neoplasma* 49:349-355, 2002; Li & Shaw *J. Biol. Chem.* 277:17397-17405, 2002; Kaur, et al., *Cell Signal* 14:419-429, 2002). For example, constitutive activation of the MK was found in T-cell childhood acute lymphoblastic leukemia (Lacronique, et al., *Science* 278: 1309-1312, 1997). Transfection of a constitutively activated STAT3 results in tumorigenicity in nude mice (Bromberg, et al., *Cell* 98:295-303, 1999). Constitutive activation of STAT3 correlates with cell proliferation in breast carcinoma (Zhang, et al., Oncogene 22:894-905, 2003) and non-small-cell lung cancer (NSCLC) (He, et al., *Biochem. Biophys. Res. Commun.* 301:386-391, 2003). On the other hand, inhibition of JAK/STAT signaling results in suppression of cancer cell growth and induces apoptosis in various cancer types (Zhang, et al., *Oncogene* 22:894-905, 2003; Blaskovich, et al., *Cancer Res.* 63:1270-1279, 2003; Yamashita, et al., *Oncogene* 22:1638-1652, 2003; Kanai, et al., *Oncogene* 22:548-554, 2003; Mora, et al., *Cancer Res.* 62:6659-6666, 2002; Buettner, et al., *Clin Cancer Res.* 8:945-954, 2002).

SOCS gene family proteins function as negative regulators of the JAK/STAT signaling pathway (O'Shea, et al., *Cell* 109 Suppl:S121-S131, 2002, Aaronson & Horvath *Science* 296: 1653-1655, 2002). Eight proteins, CIS and SOCS1-SOCS7, have been identified in the suppressors of cytokine signaling (SOCS) family. They contain a central SH2 domain, a conserved C-terminus (the SOCS box), and a unique N-terminus (Masuhara, et al., *Biochem. Biophys. Res. Commun.* 239:439-446, 1997; Hilton, et al., *Proc. Natl. Acad. Sci. USA* 95:114-119, 1998; O'Shea, et al., *Cell* 109 Suppl:S121-S131, 2002). Expression of SOCS-1 to -3 and CIS is induced by cytokine or growth factor stimulation, which directly antagonizes STAT activation as part of a classic feedback loop (O'Shea, et al., *Cell* 109 Suppl:S121-S131, 2002, Aaronson & Horvath *Science* 296:1653-1655, 2002). Ectopic expression of SOCS-1 gene has been shown to be able to block the transforming activity of oncogenic forms of JAK, in addition to its physiology role in inhibiting cytokine signaling (Frantsve, et al., *Mol. Cell. Biol.* 21:3547-3557, 2001).

Aberrant hypermethylation of promoter regions in CpG islands has been shown to be associated with transcriptional silencing of the genes in various cancers (Laird, *Nat. Rev. Cancer* 3:253-266, 2003). For example, such hypermethylation has been recognized as a mechanism for inactivating various tumor suppressor genes in cancer (Jaenisch & Bird, *Nat. Genet.* 33 Suppl:245-254, 2003; Esteller, et al., *Science* 297:1807-1808, 2002). These gene include VHL (Herman, et al., *Proc. Natl. Acad. Sci. USA* 91:9700-9704; 1994), MGMT (Esteller, et al, *Cancer Res.* 59:793-797, 1999), MLH1 (Herman, et al., *Proc. Natl. Acad. Sci. USA* 95:6870-6875, 1998), DAPK1 (Katzenellenbogen, et al, *Blood* 93:4347-4353, 1999) and SFRPs (Suzuki, et al., *Nat. Genet.* 31:141-149, 2002). Recently, involvement of SOCS-1 in carcinogenesis has also been reported. SOCS-1 was found frequently silenced by hypermethylation in hapatocellular carcinoma (HCC) (Yoshikawa, et al., *Nat. Genet.* 28:29-35, 2001), multiple myeloma (Galm, et al., *Blood* 101:2784-2788, 2003) and hepatoblastomas (Nagai, et al., *J. Hum. Genet.* 48:65-69, 2003). SOCS-1 appears to have tumor suppressor activity (Rottapel, et al., *Oncogene* 21:4351-4362, 2002) and restoration of the SOCS-1 gene in HCC cells causes growth suppression and induction of apoptosis (Yoshikawa, et al., *Nat. Genet.* 28:29-35, 2001). However, the prior art has not shown that SOCS-3 play a role in cancers such as lung cancer or breast and cancer and moreover, has not shown a role of methylation of SOCS3 in cancer.

BRIEF SUMMARY OF THE INVENTION

This invention is based on the discovery that frequent hypermethylation in CpG islands of the functional SOCS-3 promoter correlates with its transcription silencing in cancer. The invention thus provides methods of diagnosing cancer based on detecting the presence of hypermethylation in the SOCS-3 promoter and/or detecting a decrease in the level of SOCS-3 mRNA or protein. Further, the invention provides methods of treating cancer by increasing the amount of SOCS-3 activity in cancer cells. Cancers that can be diagnosed and/or treated using the methods of the invention include lung cancer, breast cancer, colorectal cancer, sarcoma, mesothelioma, prostate cancer, pancreatic cancer, a cervical cancer, ovarian cancer, gastric cancer, esophageal cancer, head and neck cancer, hepatocellular carcinoma, melanoma, glioma, or glioblastoma.

Thus, in one aspect, the invention provides methods of detecting cancer n a patient. In one embodiment, the method comprises: determining the level of a transcript encoding SEQ ID NO:2 in a biological sample from the patient; and detecting a decrease in the level of the transcript relative to normal, thereby detecting the presence of cancer in the patient. In one embodiment, the step of determining the level of the transcript comprises determining the level of the transcript comprises an amplification reaction.

In another embodiment, the method comprises: determining the level of a polypeptide having the sequence set forth in SEQ ID NO:2 in a biological sample from the patient: and detecting an increase in the level of the polypeptide relative to normal, thereby detecting the presence of cancer in the patient. In one embodiment, the step of determining the level of the polypeptide comprises performing an immunoassay.

Alternatively, cancer can be detected using a method comprising: determining the amount of methylation of a SOCS-3 promoter in a biological sample from the patient; and detecting an increase in the amount of methylation of the sample relative to normal, thereby detecting the presence of cancer in the patient. The amount of methylation can be detected using any technique known in the art, e.g., bisulfite sequences, methylation-specific PCR, or using methylation-sensitive restriction enzymes.

Cancers that can be detected using the methods of the invention include, but are not limited to, lung cancer, breast cancer, mesothelioma, colon cancer, or sarcoma.

In another aspect, the invention provides a method of monitoring the efficacy of a therapeutic treatment of cancer, the method comprising the steps of: (i) providing a biological sample from a patient undergoing the therapeutic treatment; and (ii) detecting the level of a polypeptide having an amino acid sequence of SEQ ID NO:2, or of a nucleic acid that encodes the polypeptide, in the biological sample compared to a level in a biological sample from the patient prior to, or earlier in, the therapeutic treatment, thereby monitoring the efficacy of the therapy.

In another embodiment, efficacy is monitored by: (i) providing a biological sample from a patient undergoing the therapeutic treatment; and (ii) detecting the level of methylation of the SOCS-3 promoter in the biological sample compared to a level in a biological sample from the patient prior to, or earlier in, the therapeutic treatment, thereby monitoring the efficacy of the therapy.

In another aspect, the invention provides a method of screening for an agent that increases SOCS-3 activity, the method comprising incubating a test compound with a cell comprising a SOCS-3 nucleic acid having at least 80% identity to SEQ ID NO:1; and selecting a compound that increases SOCS-3 activity, thereby identifying an agent that increases SOCS-3 activity. In one embodiment, the SOCS-3 nucleic acid sequence further comprises a hypermethylated promoter.

In one embodiment, the method of screening further comprises a step of determining the amount of methylation of the SOCS-3 promoter following incubation with the test compound.

In additional embodiments, the increase in SOCS-3 activity can be detected by measuring the levels of SOCS-3 mRNA or protein.

In another aspect, the invention provides a method of inhibiting proliferation of a cancer cell, the method comprising administering an agent that increases SOCS-3 activity to the cancer cell. In one embodiment, the cancer cell has a hypermethylated SOCS-3 promoter. Examples of cancer cells that can be inhibited include lung cancer cells, breast cancer cells, mesothelioma cells, colon cancer cells, and sarcoma cells. Inhibitory agents include, but are not limited to, an expression vector encoding SOCS-3 or a demethylating agent.

BRIEF DESCRIPTION OF THE DRAWINGS

FIG. 7 provides exemplary data showing that aberrant methylation of SOCS-3 is common in mesothelioma. The panel shows MSP analysis in primary tissue. Bands labeled 'u' indicate amplified DNA product with unmethylation specific primers. Bands labeled 'M' indicate amplified DNA products with methylation specific primers.

DETAILED DESCRIPTION OF THE INVENTION

Definitions

Figure 1A:
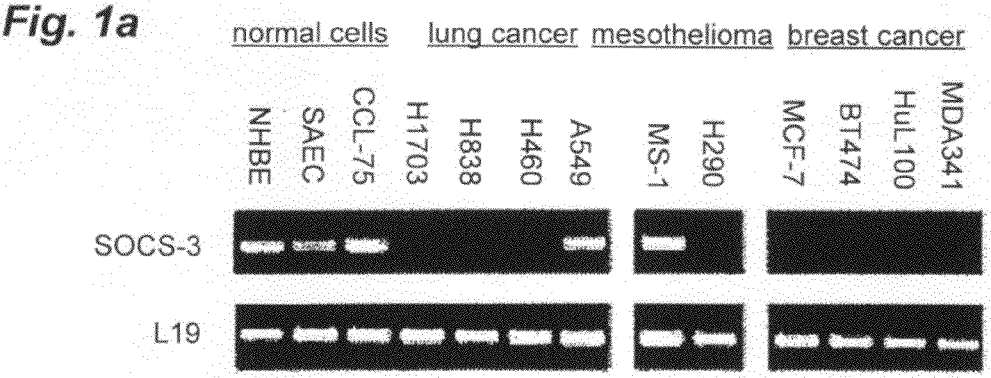
FIG. 1 shows exemplary data showing the correlation of methylation in the SOCS-3 promoter region with silencing of the SOCS-3 gene in cell lines. Panel a is RT-PCR result from four NSCLC, two mesothelioma, four breast cancer cell lines and three normal cells. The fragment of human SOCS-3 cDNA amplified is 579 bp. A 395 by fragment of the L19 ribosomal protein gene is used as a positive control for RNA quality and loading. Panel b is a scheme of the 5' SOCS-3 promoter region and SOCS-3 gene. The large black bar represents the open reading frame of SOCS-3 gene with an arrow on top indicating the translation start site. Vertical bars represent CpG islands. The line and double arrow below the CpG islands represent regions analyzed by MSP and bisulfite sequencing, respectively. Panel c is MSP analysis of cell lines. Bands (298 bp) in lanes labeled "U" are unmethylated DNA product amplified with unmethylation-specific primers. Bands (268 bp) in lanes labeled "M" are methylated DNA product amplified with methylation-specific primers.

The term "SOCS-3" refers to nucleic acid and polypeptide polymorphic variants, alleles, mutants, and interspecies homologues that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 20, 50, 100, 200, 500, 1000, or more amino acids, to a sequence of SEQ ID NO:2; (2) bind to antibodies, e.g., polyclonal antibodies, raised against an immunogen comprising an amino acid sequence of SEQ ID NO:2, or conservatively modified variants thereof; (3) specifically hybridize under stringent hybridization conditions to a nucleic acid sequence of SEQ ID NO:1, or conservatively modified variants thereof; or (4) or have a nucleic acid sequence that has greater than about 90%, preferably greater than about 96%, 97%, 98%, 99%, or higher nucleotide sequence identity, preferably over a region of over a region of at least about 30, 50, 100, 200, 500, 1000, or more nucleotides, to SEQ ID NO:1; or (5) have at least 25, often 50, 75, 100, 150, 200, 250, 300, 350, 400 or more contiguous amino acid of SEQ ID NO:2; or at least 25, often 50, 75, 100, 150, 200, 250, 300, 350, 400, 500, or more contiguous nucleotides of SEQ ID NO:1. A SOCS-3 polynucleotide or polypeptide sequence is typically from a human, but may be from other mammals, but not limited to, a non-human primate, a rodent, e.g., a rat, mouse, or hamster; a cow, a pig, a horse, a sheep, or other mammal. A "SOCS-3" polypeptide and a "SOCS3" polynucleotide include both naturally occurring or recombinant forms. Exemplary SOCS-3 are provided herein and are known in the art (see, e.g., accession numbers NP_003946, NP_031733, and NP_446017 for human, mouse and rat protein sequences, respectively; and accession numbers NM_003955.2, NM_007707.2, and NM_053565.1 for human, mouse, and rat polynucleotide sequences, respectively).

A "full length" SOCS-3 protein or nucleic acid refers to a SOCS-3 polypeptide or polynucleotide sequence, or a variant thereof, that contains all of the elements normally contained in one or more naturally occurring, wild type SOCS-3 polynucleotide or polypeptide sequences. The "full length" may be prior to, or after, various stages of post-translation processing or splicing, including alternative splicing.

The term "hypermethylation" refers to methylation of cytosine at a position that is normally unmethylated in the SOCS-3 gene sequence, e.g., the SOCS-3 promoter. As appreciated by one of skill in the art, detection of hypermethylation in a region of the SOCS-3 gene such as the promoter does not require that every CpG residue in the promoter be analyzed. One or more CpG residues may be the target in a methylation analysis.

The "SOCS-3 promoter" refers to a sequence comprising regulatory regions that control transcription of "SOCS-3". An exemplary human SOCS-3 promoter sequence comprises the nucleotide sequence set forth in SEQ ID NO:3. A SOCS-3 promoter sequence typically comprises STAT-binding sites, a G-rich region and a TAT box sequence as shown in SEQ ID NO:3. These regulatory regions are conserved between human and mouse SOCS-3 promoter regions.

"Biological sample" as used herein is a sample of biological tissue or fluid that contains nucleic acids or polypeptides, e.g., of a breast cancer protein, polynucleotide or transcript. Such samples are typically from humans, but include tissues isolated from non-human primates, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, will be particularly useful.

The "level of SOCS-3 mRNA" in a biological sample refers to the amount of mRNA transcribed from a SOCS-3 gene that is present in a cell or a biological sample. The mRNA generally encodes a functional SOCS-3 protein, although mutations may be present that alter or eliminate the function of the encoded protein. A "level of SOCS-3 mRNA" need not be quantified, but can simply be detected, e.g., a subjective, visual detection by a human, with or without comparison to a level from a control sample or a level expected of a control sample.

The "level of SOCS-3 protein or polypeptide" in a biological sample refers to the amount of polypeptide translated from SOCS-3 mRNA that is present in a cell or biological sample. The polypeptide may or may not have SOCS-3 protein activity. A "level of SOCS-3 protein" need not be quantified, but can simply be detected, e.g., a subjective, visual detection by a human, with or without comparison to a level from a control sample or a level expected of a control sample.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be large negative numbers, e.g., 5, 10, 20, 30, 40, 40, 70, 90, 110, 150, 170, etc.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like (see, e.g., the American Type Culture Collection catalog or web site, www.atcc.org).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Value (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor & Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the noncovalent association of independent tertiary units.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g. to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J.

Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Eghoim, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeff's et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the breast cancer nucleic acids, proteins and antibodies at any position. Any method known in the art for conjugating the antibody to the label may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem and Cytochem.,* 30:407 (1982).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990)*PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

By "determining the functional effect" is meant assaying for a compound that increases or decreases a parameter that is indirectly or directly under the influence of SOCS-3, e.g., functional, enzymatic, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties for the protein, measuring inducible markers or transcriptional activation of the SOCS-3 protein; measuring binding activity, e.g., binding to JAK, measuring cellular proliferation, measuring apoptosis, or measuring STAT kinase activity. Determination of the functional effect of a compound on cancer can also be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in SOCS-3 RNA or protein levels, measurement of RNA stability, identification of downstream or reporter gene expression (CAT, luciferase, β-gal, GFP and the like), e.g., via chemiluminescence, fluorescence, colorimetric reactions, antibody binding, inducible markers, and ligand binding assays. "Functional effects" include in vitro, in vivo, and ex vivo activities.

"Activators" or "modulators" of SOCS-3 polynucleotide and polypeptide sequences are used to refer to agents that activate SOCS-3. Activators are agents that, e.g., induce or activate the expression of a polypeptide of the invention or bind to, stimulate, increase, open, activate, facilitate, or enhance activation, sensitize or up regulate the activity of a polypeptide of the invention. Activators include nucleic acids that encode SOCS-3, demethylating compounds, as well as naturally occurring and synthetic compounds, small chemical molecules and the like. Assays for activators include, e.g., applying candidate compounds to cells expressing SOCS-3 and then determining the functional effects. Samples or assays comprising SOCS-3 that are treated with a potential activator are compared to control samples without the activator to examine the extent of effect. Control samples (untreated with candidate agents) are assigned a relative activity value of 100%. Activation of the polypeptide is achieved when the polypeptide activity value relative to the control is 110%, optionally 150%, optionally 200, 300%, 400%, 500%, or 1000-3000% or more higher.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 (3$^{rd}$ ed. 1994).

"Tumor cell" refers to precancerous, cancerous, and normal cells in a tumor.

"Cancer cells," "transformed" cells or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3$^{rd}$ ed. 1994)).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, *Fundamental Immunology*.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$, may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, Nature 256:495-497 (1975); Kozbor et al., *Immunology Today* 4:72 (1983); Cole et al., pp. 77-96 in *Monoclonal Antibodies and Cancer Therapy* (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Identification of SOCS-3 Sequences in a Sample from a Patient

In one aspect of the invention, the levels of SOCS-3 mRNA or protein are determined in patient samples for which diagnostic or prognostic information is desired. That is, normal tissue (e.g., normal lung, breast or other tissue) may be distinguished from cancerous or metastatic cancerous tissue from the same source; or cancer tissue or metastatic cancerous tissue can be compared with similar tissue samples from other patients, e.g., surviving cancer patients.

General Recombinant DNA Methods

This invention relies on routine techniques in the field of recombinant genetics. Basic texts disclosing the general methods of use in this invention include Sambrook & Russell, *Molecular Cloning, A Laboratory Manual* (3rd Ed, 2001); Kriegler, *Gene Transfer and Expression: A Laboratory Manual* (1990); and *Current Protocols in Molecular Biology* (Ausubel et al., eds., 1994-1999). Methods that are used to produce SOCS-3 for use in the invention may also be employed to produce protein ligands or polypeptides that modulate ligand binding to the receptor, for use in the invention.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoraraidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

Cloning Methods for the Isolation of Nucleotide Sequences

In general, nucleic acid sequences encodingSOCS-3 and related nucleic acid sequence homologs are cloned from cDNA and genomic DNA libraries by hybridization with a probe, or isolated using amplification techniques with oligonucleotide primers. For example, sequences are typically isolated from mammalian nucleic acid (genomic or cDNA) libraries by hybridizing with a nucleic acid probe, the sequence of which can be derived from SEQ ID NO:1.

Amplification techniques using primers can also be used to amplify and isolate nucleic acids from DNA or RNA (see, e.g., section "detection of polynucleotides", below). Suitable primers for amplification of specific sequences can be designed using principles well known in the art (see, e.g., Dieffenfach & Dveksler, *PCR Primer: A Laboratory Manual* (1995)). These primers can be used e.g., to amplify either the full length sequence or a probe, typically varying in size from ten to several hundred nucleotides, which is then used to identify SOCS-3 polynucleotides.

Nucleic acids encoding SOCS-3 can also be isolated from expression libraries using antibodies as probes. Such polyclonal or monoclonal antibodies can be raised using the sequence of SEQ ID NO:2.

Synthetic oligonucleotides can also be used to construct SOCS-3 genes for use as probes or for expression of protein. This method is performed using a series of overlapping oligonucleotides usually 40-120 by in length, representing both the sense and nonsense strands of the gene. These DNA fragments are then annealed, ligated and cloned. Alternatively, amplification techniques can be used with precise primers to amplify a specific subsequence of the nucleic acid. The specific subsequence is then ligated into an expression vector.

The nucleic acid encoding SOCS-3 is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising SOCS-3 or domains thereof can be made according to standard techniques. For example, a domain such as ligand binding domain can be covalently linked to a heterologous protein., e.g., green fluorescent protein, luciferase, or β-gal.

Expression in Prokaryotes and Eukaryotes

To obtain high level expression of a SOCS-3 nucleic acid, one typically subclones a SOCS-3 nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook & Russell, supra, Ausubel et al, supra. Bacterial expression systems for expressing the SOCS-3 protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the SOCS-3-encoding nucleic acid in host cells. A typical expression cassette thus contains a promoter operably linked to the nucleic acid sequence encoding SOCS-3 and signals required for efficient polyadenylation of the transcript, ribosome binding sites, and translation termination. The nucleic acid sequence encoding SOCS-3 may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a SOCS-3-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of SOCS-3 protein, which are then purified using standard techniques (see, e.g., Colley et al., *J. Biol. Chem.* 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell, supra). It is only necessary that the particular genetic engineering procedure used be capable of successfully introducing at least one gene into the host cell capable of expressing SOCS-3.

After the expression vector is introduced into the cells, the transfected cells are cultured under conditions favoring expression of SOCS-3, which is recovered from the culture using standard techniques (see, e.g., Scopes, *Protein Purification: Principles and Practice* (1982); U.S. Pat. No. 4,673,641; Ausubel et al., supra; and Sambrook et al., supra).

Detection of Cancer
Detection of SOCS-3 polynucleotides and polypeptides

Typically, the level of a SOCS-3 polynucleotide or polypeptide will be detected in a biological sample. A "biological sample" refers to a cell or population of cells or a quantity of tissue or fluid from an animal. Most often, the sample has been removed from an animal, but the term "biological sample" can also refer to cells or tissue analyzed in vivo, i.e., without removal from the animal. Typically, a "biological sample" will contain cells from the animal, but the term can also refer to noncellular biological material, such as noncellular fractions of blood, saliva, or urine, that can be used to measure the cancer-associated polynucleotide or polypeptide levels. Numerous types of biological samples can be used in the present invention, including, but not limited to, a tissue biopsy, a blood sample, a buccal scrape, a saliva sample, or a nipple discharge.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

Detection of Hypermethylated Sequences

In one embodiment, a cancer cell, e.g., a lung cancer or breast cancer cell, is detected by detecting the presence of hypermethylation of the SOCS-3 promoter. The degree of methylation can be detected using a variety of methods. For example, methylation analysis can be performed using Southern hybridization, which assesses methylation-sensitive restriction sites within CpG islands of the SOCS-3 promoter. Any restriction endonuclease that includes CG as part of its recognition site and that is inhibited when the C is methylated, can be utilized for this analysis. Methylation sensitive restriction endonucleases include AciI, BsiEI, BssHII, BstUI, Eag I, FauI, HaeII, HpaI, HpaII, MspI, NarI, NotI, SacII, or SmaI. These enzymes may be used alone or in combination.

More sensitive assays for mapping DNA methylation patterns are also available. These include bisulfite DNA sequencing and methylation-specific PCR. These techniques allow analysis of multiple CpG dinucleotides across a single CpG island of interest. Bisulfite DNA sequencing is based on bisulfite-induced modification of genomic DNA under conditions whereby unmethylated cytosine is converted to uracil. The bisulfite-modified sequence is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced directly or can be cloned and sequenced to provide methylation maps of single DNA molecules (see, e.g., Frommer, et al., *Proc. Natl. Acad. Sci.* 89: 1827-1831, 1992).

Methylation-specific PCR can also be used to assess the methylation status of CpG dinucleotide sites within a CpG island, independent of the use of methylation-sensitive restriction enzymes. This assay involves the initial modification of DNA by sodium bisulfite, or another comparable agents, to convert unmethylated, but not methylated, cytosines to uracils. Subsequent amplification with primers specific for methylated DNA, or unmethylated DNA, results in the amplification of DNA consisting of methylated CpG dinucleotides. The primers specifically distinguish between u methylated and non-methylated DNA. To accomplish this, primer sequences are typically chosen for regions containing frequent cytosines (to distinguish unmodified from modified DNA), and CpG pairs near the 3' end of the primers (to provide maximal discrimination in the PCR reaction between methylated and unmethylated DNA). Since the two strands of DNA are no longer complementary after bisulfite treatment, primers can be designed for either modified strand. For example, primers specific for the methylated DNA typically have a T in the 3' CG pair to distinguish it from the C retained in methylated DNA, and the complement is designed for the antisense primer. See U.S. Pat. No. 5,786,146; Herman et al., *Proc. Natl. Acad. Sci. USA* 93: 9821-9826 (1996).

In some embodiments, SOCS-3 promoter region sequences from −1005 to −983 and −754 to −737 are evaluated. As appreciated by one of skill in the art, any region of the promoter can be used for analysis, as long as it contains methylated CpG residues. In some embodiments, the regions can contain 1-3 CpG islands. Methylated CpG islands can be determined using any of the techniques known in the art, such as those described above.

Detection of SOCS-3 mRNA

In one embodiment, the presence of cancer is evaluated by determining the level of expression of mRNA encoding SOCS-3. Methods of evaluating RNA expression of a particular gene are well known to those of skill in the art, and include, inter alia, hybridization and amplification based assays.

Direct Hybridization-Based Assays

Methods of detecting and/or quantifying the level of SOCS3 gene transcripts (mRNA or cDNA made therefrom) using nucleic acid hybridization techniques are known to those of skill in the art. For example, one method for evaluating the presence, absence, or quantity of SOCS3 polynucleotides involves a Northern blot. Gene expression levels can also be analyzed by techniques known in the art, e.g., dot blotting, in situ hybridization, RNase protection, probing DNA microchip arrays, and the like.

Amplification-Based Assays

In another embodiment, amplification-based assays are used to measure the expression level of SOCS-3. In such an assay, the SOCS nucleic acid sequences act as a template in an amplification reaction (e.g., Polymerase Chain Reaction, or PCR). In a quantitative amplification, the amount of amplification product will be proportional to the amount of template in the original sample. Comparison to appropriate controls provides a measure of the level of SOCS-3 in the sample. Methods of quantitative amplification are well known to those of skill in the art. Detailed protocols for quantitative PCR are provided, e.g., in Innis et al. (1990)*PCR Protocols, A Guide to Methods and Applications*, Academic Press, Inc. N.Y.). The known nucleic acid sequences for SOCS-3 (see, e.g., SEQ ID NO:1) is sufficient to enable one of skill to routinely select primers to amplify any portion of the gene.

In one embodiment, a TaqMan based assay is used to quantify the cancer-associated polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace (1989) Genomics 4:560, Landegren et al. (1988) *Science* 241: 1077, and Barringer et al. (1990) Gene 89:117), transcription amplification (Kwok et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

Production of Antibodies and Immunological Detection SOCS-3

Antibodies can also be used to detect SOCS-3. Antibodies to SOCS-3 are commercially available (e.g., Santa Cruz Biotechnology) or can be produced using well known techniques (see, e.g., Harlow & Lane, Antibodies: A Laboratory Manual (1988) and Harlow & Lane, *Using Antibodies* (1999); Coligan, *Current Protocols in Immunology* (1991); Goding, *Monoclonal Antibodies: Principles and Practice* (2d ed. 1986); and Kohler & Milstein, *Nature* 256:495-497 (1975)). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)). Such antibodies are typically used for diagnostic or prognostic applications, e.g., in the detection of lung or breast cancer.

SOCS-3 or a fragment thereof may be used to produce antibodies specifically reactive with SOCS-3. For example, a recombinant SOCS-3 or an antigenic fragment thereof, is isolated as described herein. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Typically, polyclonal antisera with a titer of $10^4$ or greater are selected and tested for their cross reactivity against non-SOCS-3 proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better. For cross-reactivity determination, typically immunoabsorbed antisera are used in a competitive binding immunoassay to compare a second protein to the SOCS3 protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the antigenic SOCS-3 protein that is required to inhibit 50% of binding, then the second protein is said to specifically bind to the polyclonal antibodies generated to the SOCS-3 immunogen.

Once SOCS-3-specific antibodies are available, binding interactions with SOCS-3 can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled SOCS-3 polypeptide or a labeled anti-SOCS-3 antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of SOCS-3 present in the sample is measured indirectly by measuring the amount of a known, added (exogenous) SOCS-3 displaced (competed away) from an anti-SOCS-3 antibody by the unknown SOCS-3 present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels, enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize SOCS-3, or secondary antibodies that recognize anti-SOCS-3.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidatases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, 10, antigen-coated particles are agglutinated by samples comprising the target antibodies. In this format, none of the components need be labeled and the presence of the target antibody is detected by simple visual inspection.

Identification Of Activators Of SOCS-3

Activators of SOCS-3, i.e., activators of SOCS-3 polypeptide or polynucleotide expression, are useful for treating cancer, e.g., lung cancer or breast cancer. Agents that activate SOCS-3 can be tested using a variety of methods. Agents that activate SOCS-3 include compounds that activate enhance SOCS-3 activity as well as agents that increase SOCS-3 expression, including demethylating agents that decrease methylation of the SOCS-3 promoter.

The agents tested as activators of SOCS-3 can be any small chemical compound, or a biological entity, such as a protein, sugar, nucleic acid or lipid. Typically, test compounds will be small chemical molecules and peptides. Essentially any chemical compound can be used as a potential activator in the assays of the invention, although most often compounds that can be dissolved in aqueous or organic (especially DMSO-based) solutions are used.

Large Scale and High Throughput Screening

The assays are designed to screen large chemical libraries by automating the assay steps and providing compounds from any convenient source to assays, which are typically run in parallel (e.g., in microtiter formats on microtiter plates in robotic assays).

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

Solid Phase and Soluble High Throughput Assays

In the high throughput assays, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

SOCS-3 can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest (e.g., SOCS-3) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, poly-His, etc.) Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody that recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:4). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent that fixes a chemical group to the surface that is reactive with a portion of the tag binder. For example, groups that are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, J. Am. Chem. Soc. 85:2149-2154 (1963) (describing solid phase synthesis of, e.g., peptides); Geysen et al., J. Immun. Meth. 102:259-274 (1987) (describing synthesis of solid phase components on pins); Frank and Doring, Tetrahedron 44:60316040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can increase the expression or activity of SOCS-3, as further described below. Control reactions that measure SOCS-3 activity of the cell in a reaction that does not include a potential modulator are optional, as the assays are highly uniform. Such optional control reactions are appropriate and increase the reliability of the assay. Accordingly, the methods of the invention typically include such a control reaction. For each of the assay formats described, "no modulator" control reactions that do not include a modulator provide a background level of binding activity.

Methods of Screening for Activators of SOCS-3

A number of different screening protocols can be utilized to identify agents that increase the level of expression or activity of SOCS-3 in cells, particularly mammalian cells, and especially human cells. In general terms, the screening methods involve screening a plurality of agents to identify an agent that increases the activity of SOCS-3 by, e.g., binding to a SOCS-3 polypeptide, by binding to a protein that SOCS-3 binds, e.g., a kinase, by preventing an inhibitor from binding to SOCS-3, by increasing association of an activator with SOCS-3, or by activating expression of SOCS-3.

Any cell expressing SOCS-3 or a fragment thereof can be used to identify activators. In some embodiments, the cells are eukaryotic cells lines transformed to express a heterologous SOCS-3 polypeptides. In some embodiments, a cell expressing an endogenous SOCS-3 is used in screens.

SOCS-3 Binding Assays

Preliminary screens can be conducted by screening for agents capable of binding to SOCS-3, as at least some of the agents so identified are likely SOCS-3 activators, or modulators that bind to endogenous proteins that interact with SOCS-3. Binding assays are also useful, e.g., for identifying endogenous proteins that interact with SOCS-3.

Binding assays usually involve contacting a SOCS-3 protein with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in Neurotransmitter Receptor Binding (Yamamura, H. I., et al., eds.), pp. 61-89. Other binding assays involve the use of mass spectrometry or NMR techniques to identify molecules bound to SOCS-3 or displacement of labeled substrates. The SOCS-3 proteins utilized in such assays can be naturally expressed, cloned or synthesized.

In addition, mammalian or yeast two-hybrid approaches (see, e.g., Bartel, P. L. et. al. Methods Enzymol, 254:241 (1995)) can be used to identify polypeptides or other molecules that interact or bind when expressed together in a host cell.

In other embodiments, agents are identified that compete with SOCS-3, or a binding fragment thereof, for binding to a protein with which SOCS-3 normally interacts, e.g., a kinase. In such an assay, the candidate compound can be added to a binding assay comprising the binding partner and SOCS-3, or a fragment thereof, either concurrently or before or after SOCS-3.

SOCS-3 Activity

SOCS-3 and its alleles and polymorphic variants play a role in inhibiting JAK/STAT signaling. SOCS3 inhibits cytokine signal transduction by binding to tyrosine kinase receptors including gp130, LIF, erythropoietin, insulin and leptin receptors. Binding to JAK2, inhibits its kinase activity. The activity of SOCS-3 polypeptides can be assessed using a variety of in vitro and in vivo assays to determine functional, chemical, and physical effects, e.g., measuring STAT kinase activity. For example, SOCS-3 binds to the activation loop of Janus kinases, inhibiting kinase activity and thereby suppressing cytokine signaling. SOCS-3 inhibits STAT3 phosphorylation by binding to JAK-proximal sites on cytokine receptors to inhibit JAK activity. Binding to JAK is mediated through the KIR and SH2 domains. Thus, any of a variety of endpoints can be used to determine SOCS-3 activity. These include, but are not limited to, measuring SOCS-3 binding to JAK, measuring STAT phosphorylation, or determining JAK activity, e.g., by measuring levels of phosphorylation of receptor tyrosine kinases. Further, cell growth and/or apoptosis can also be used to assess SOCS-3 activity. Methodology for conducting these assays is well known in the art (see, e.g., Masuhara et al., *Biochem. Biophys. Res. Commun.* 239: 439-446, 1997; Minamoto, et al, *Biochem. Biophys. Res. Commun.* 237:79-83, 1997).

In one embodiment, SOCS-3 activity can be determined by measuring cell viability. Cell viability may be assessed by measuring many different endpoints including levels of cytoplasmic enzymes, permeability of cells to dyes, DNA fragmentation, release of a radioisotopic label such as $^{51}$Cr or other formats. Typically, cell viability is measured using an assay suitable for a high throughput screening format, such as a colorimetric or fluorescent viability assay. For example, an Alamar blue (AB) assay, incorporates a redox indicator that changes the color or fluorescence in response to metabolic activity. The Alamar blue fluoresces in the presence of living, but not dead, cells. Such an assay can be conveniently read in a microplate or by flow cytometry. Colorimetric assays such as the MTT assay, which measures the reduction of MTT (3-(4.5-dimethyl) thiazol-2-yl-2,5-diphenyl tetrazolium bromide) to formazan, may also be used conveniently in a high throughput format to measure cell viability and proliferation.

Other assays that measure cell number may also be used. These include assays that measure intercalation of dyes into the DNA of a cell. The amount of intercalated dye is directly proportional to cell number. For example, cells can be stained with a dye such as Hoechst 33342, which intercalates in the DNA of vital cell, an cell number determined by measuring the amount of fluorescence. Cells may also be directly counted.

Samples or assays that are treated with a potential SOCS-3 activator are compared to control samples without the test compound, to examine the extent of modulation. Control samples (untreated with activators) are assigned a relative SOCS-3 activity value of 100. Activation of SOCS-3 is achieved when the SOCS-3 activity value relative to the control is 110%, optionally 150%, 200%, 300%, 400%, 500%, or 1000-2000%.

Expression Assays

Screening assays for a compound that increases the expression of SOCS-3 are also provided. Screening methods generally involve conducting cell-based assays in which test compounds are contacted with one or more cells capable of expressing SOCS-3, and then detecting an increase in SOCS-3 expression (either transcript or translation product). Assays can be performed with any cells that express SOCS-3.

SOCS-3 expression can be detected in a number of different ways. As described infra, the expression level of SOCS-3 in a cell can be determined by probing the mRNA expressed in a cell with a probe that specifically hybridizes with a transcript (or complementary nucleic acid derived therefrom) of SOCS-3. Probing can be conducted by lysing the cells and conducting Northern blots or without lysing the cells using in situ-hybridization techniques. Alternatively, SOCS-3e protein can be detected using immunological methods in which a cell lysate is probed with antibodies that specifically bind to SOCS-3.

Other cell-based assays involve reporter assays conducted with cells using standard reporter gene assays. These assays can be performed in either cells that do, or do not, express SOCS-3. Some of these assays are conducted with a heterologous nucleic acid construct that includes a SOCS-3 promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, CAT (chloramphenicol acetyl transferase; Alton and Vapnek (1979) Nature 282:864-869), luciferase, ÿ-galactosidase and alkaline phosphatase (Toh, et al. (1980) Eur. J. Biochem. 182:231-238; and Hall et al. (1983) J. Mol. Appl. Gen. 2:101).

In these assays, cells harboring the reporter construct are contacted with a test compound. Modulated promoter expression is monitored by detecting the level of a detectable reporter. A number of different kinds of SOCS-3 activators can be identified in this assay. For example, a test compound that inhibits the promoter by binding to it, inhibits the promoter by binding to transcription factors or other regulatory factors, binds to their promoter or triggers a cascade that produces a molecule that inhibits the promoter can be identified. Similarly a test compound that, e.g., activates the promoter by binding to it, activates the promoter by binding to transcription factors or other regulatory factors, binds to their promoter or triggers a cascade that produces a molecule that activates the promoter can also be identified.

The level of expression or activity can be compared to a baseline value. The baseline value can be a value for a control sample or a statistical value that is representative of SOCS-3expression levels for a control population (e.g., lean individuals as described herein) or cells (e.g., tissue culture cells not exposed to a SOCS-3 modulator). Expression levels can also be determined for cells that do not express SOCS-3 as a negative control. Such cells generally are otherwise substantially genetically the same as the test cells.

Various controls can be conducted to ensure that an observed activity is authentic including running parallel reactions with cells that lack the reporter construct or by not contacting a cell harboring the reporter construct with test compound. Compounds can also be further validated as described below.

Compounds can increase expression of SOCS-3 by a variety of mechanisms. For example, in one embodiment, compounds may increase expression by decreasing methylation of the SOCS-3 promoter. Such compounds include methylation suppressive reagents such as 5-azacytadine and the like, which can be introduced into a cell.

Nucliec Acids that Increase SOCS-3 Activity

In one aspect of the present invention, SOCS-3 activators can also comprise nucleic acid molecules that express SOCS-3. Conventional viral and non-viral based gene transfer methods can be used to introduce nucleic acids encoding SOCS-3 polypeptides in mammalian cells or target tissues. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

Non-Viral Delivery Methods

Methods of non-viral delivery of nucleic acids encoding engineered polypeptides of the invention include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectarm™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Methods

The use of RNA or DNA viral based systems for the delivery of SOCS-3 nucleic acids is known in the art. Conventional viral based systems for include retroviral, lentivirus, adenoviral, adeno-associated and herpes simplex virus vectors for gene transfer.

In many gene therapy applications, it is desirable that the gene therapy vector be delivered with a high degree of specificity to a particular tissue type, e.g., lung tissue or breast tissue. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism, transfected with SOCS-3 nucleic acids and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

In some embodiments, SOCS-3 polypeptides and polynucleotides can also be administered as vaccine compositions to stimulate an immune response, typically a cellular (CTL and/or HTL) response. Such vaccine compositions can include, e.g., lipidated peptides (see, e.g., Vitiello, A. et al., *J. Clin. Invest.* 95:341 (1995)), peptide compositions encapsulated in poly(DL-lactide-co-glycolide) ("PLG") microspheres (see, e.g., Eldridge, et al., *Molec. Immunol.* 28:287-294, (1991); Alonso et al., *Vaccine* 12:299-306 (1994); Jones et al., *Vaccine* 13:675-681 (1995)), peptide compositions contained in immune stimulating complexes (ISCOMS) (see, e.g., Takahashi et al., *Nature* 344:873-875 (1990); Hu et al., *Clin Exp Immunol.* 113:235-243 (1998)), multiple antigen peptide systems (MAPs) (see, e.g., Tam, *Proc. Natl. Acad. Sci. U.S.A.* 85:5409-5413 (1988); Tam, *J. Immunol. Methods* 196:17-32 (1996)), peptides formulated as multivalent peptides; peptides for use in ballistic delivery systems, typically crystallized peptides, viral delivery vectors (Perkus, et al., In: *Concepts in vaccine development* (Kaufmann, ed., p. 379, 1996); Chakrabarti, et al., *Nature* 320:535 (1986); Hu et al., *Nature* 320:537 (1986); Kieny, et al., *AIDS Bio/Technology* 4:790 (1986); Top et al., *J. Infect. Dis.* 124:148 (1971); Chanda et al., *Virology* 175:535 (1990)), particles of viral or synthetic origin (see, e.g., Kofler et al., *J. Immunol. Methods.* 192:25 (1996); Eldridge et al., *Sem. Hematol.* 30:16 (1993); Falo et al., *Nature Med.* 7:649 (1995)), adjuvants (Warren et al., *Annu. Rev. Immunol.* 4:369 (1986); Gupta et al., *Vaccine* 11:293 (1993)), liposomes (Reddy et al., *J. Immunol.* 148: 1585 (1992); Rock, *Immunol. Today* 17:131 (1996)), or, naked or particle absorbed cDNA (Ulmer, et al., *Science* 259:1745 (1993); Robinson et al., *Vaccine* 11:957 (1993); Shiver et al., In: *Concepts in vaccine development* (Kaufmann, ed., p. 423, 1996); Cease & Berzofsky, *Annu. Rev. Immunol.* 12:923 (1994) and Eldridge et al., *Sem. Hematol.* 30:16 (1993)). Toxin-targeted delivery technologies, also known as receptor mediated targeting, such as those of Avant Immunotherapeutics, Inc. (Needham, Mass.) may also be used.

Administration of Pharmaceutical and Vaccine Compositions

Activators of SOCS-3 can be administered to a patient for the treatment of cancer, e.g., lung cancer or breast cancer. As described in detail below, the activators are administered in any suitable manner, optionally with pharmaceutically acceptable carriers.

The identified activators can be administered to a patient at therapeutically effective doses to prevent, treat, or control cancer. The compounds are administered to a patient in an amount sufficient to elicit an effective therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular SOCS-3 activator employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multidose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Kits for Use in Diagnostic and/or Prognostic Applications

For use in diagnostic, research, and therapeutic applications suggested above, kits are also provided by the invention. In the diagnostic and research applications such kits may include any or all of the following: assay reagents, buffers, SOCS-3-specific nucleic acids or antibodies, hybridization probes and/or primers, SOCS-3 expression constructs, small molecule activators of SOCS-3 etc. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of SOCS-3 activity. Such kits can be prepared from readily available materials and reagents. For example, such kits can comprise one or more of the following materials: a SOCS-3 polypeptide or polynucleotide, reaction tubes, and instructions for testing SOCS-3activity. Optionally, the kit contains biologically active SOCS-3 protein. A wide variety of kits and components can be prepared according to the present invention, depending upon the intended user of the kit and the particular needs of the user.

A diagnostic kit may comprise methylation-specific and/or primers specific for unmethylated sequences. Examples of methylation-specific primer are 5'-TATATATTCGC-GAGCGCGGTTT-3' (SEQ ID NO:5) (forward) and 5'-CGCTGCGCCCAGATGTT-3' (SEQ ID NO:6) (reverse), corresponding to the SOCS-3 promoter region sequences -1005 to -983 and -754 to -737, respectively. Sequences of the unmethylation-specific primers were: 5'-TGTGGTGGT TGTTTATATATTTGTGAGTGTGGTT-3' (SEQ ID NO:7) (forward) and 5'-CAACCAACAATAACCCACACTACAC-CCA-3'(SEQ ID NO:8) (reverse), corresponding to the SOCS-3 promoter region sequences -1018 to -984 and -748 to -720, respectively. Thus kits of the invention can comprises these primers or other primers that target the same CpG islands or other CpG islands that are methylated in cancer.

EXAMPLES

Materials and Methods
Cell Lines and Tissue Samples

Human NSCLC cell lines (NCI-H1703, NCI-H460, NCI-H838 and NCI-A549), a normal lung cell line (CCL-75, fibroblast), and human breast cancer cell lines (MCF-7, HuL100, BT474 and MDA341) were obtained from American Type Culture Collections (ATCC) (Manassas, Va.). Human mesothelioma cancer cell lines NCI-H290 and MS-1 were obtained from NIH (Frederick, Md.). These cells, except CCL-75, were cultured in RPMI 1640 supplemented with 10% foetal bovine serum, penicillin (100 IU/ml) and streptomycin (100 mg/ml). CCL-75 was cultured in MEM with Earle's BSS containing 2 mM L-glutamine, 1.0 mM sodium pyruvate, 0.1 mM nonessential amino acids, 1.5 g/L sodium bicarbonate and 10% fetal bovine serum. Normal human small airway epithelial cells (SAEC) and bronchial epithelial cells (NHBE) were obtained from Clonetics (Walkersville, Md.) and cultured in Clonetics SAGMTM Bullet Kit. All cells were cultured at 37° C. in a humid incubator with 5% $CO_2$.

Fresh lung cancer tissue and adjacent normal lung tissue from patients undergoing resection of early stage lung cancers were collected at the time of surgery, and immediately snap-frozen in liquid nitrogen. These tissue samples were kept at −170° C. in a liquid nitrogen freezer before use.

Northern Blotting and Semi-Quantitative RT-PCR

Total RNA from lung cancer cell lines, fresh lung cancer and paired adjacent normal tissue were isolated using TRIzol reagent (Life Technologies, Carlsbad, Calif.). Poly (A) RNA of those samples were isolated further from the total RNA using Oligotex mRNA Kit (Qiagen Inc., Valencia, Calif.). SOCS-3 cDNA insert from the cDNA construct in pCDNA3 vector was used as a probe for Northern blot. Northern blotting was carried out as described previously (26). The same membrane was then re-probed with a specific probe of L19 ribosomal protein as a standard. RT-PCR was performed in GeneAmp PCR system 9700 using One-step RT-PCR Kit from Life Technologies Inc., according to the manufacture's protocol. Primers for RT-PCR were obtained from Operon Technologies Inc. (Alameda, Calif.). Primer sequences for a 579 by fragment of the human SOCS-3 cDNA were: 5'-GTCACCCACAGCAAGTTTCC-3' (SEQ ID NO:9) (forward) and 5'-CCGACAGAGATGCTG AAGAG-3' (SEQ ID NO:10) (reverse). A 395 by fragment of a gene encoding the L19 ribosomal protein was used as an internal control.

Western Blotting

Standard protocol was used for western blot analysis. Anti-phospho-Stat3 (Tyr705) rabbit polyclonal antibody and Anti-β-actin mouse monoclonal antibody were obtained from Cell Signaling Technology (Beverly, Mass.). Anti-human SOCS-3 mouse monoclonal antibody was obtained from IBL Co., LTD. (Gunma, Japan).

Sequencing Analysis

Genomic DNA from the cell lines and fresh tissue samples was extracted using DNA STAT-60TM reagent (TEL-TEST, Inc., Friendswood, Tex.), according to the manufacture's protocol. Bisulfite-modified genomic DNA was amplified using primers (5'-GTGTAGAGTAGTGATTAAATA-3' (SEQ ID NO:11) (forward) and 5'-TCCTTAAAACTAAACCCCCTC-3' (SEQ ID NO:12) (reverse)) designed to amplify nucleotides -1084 to -671 of the SOCS-3 promoter region (the start codon ATG of SOCS-3 is defined as +1). The PCR products were cloned into TOPO-TA pCR2.1 vector (Life Technologies) and multiple randomly picked clones from each sample were sequenced using standard techniques.

Methylation-Specific PCR

Bisulfite-treated genomic DNA was amplified using either a methylation-specific or unmethylation-specific primer set. HotStarTaq DNA polymerase (Qiagen Inc.) was used in the experiments. Sequences of the methylation-specific primers were: 5'-TATATATTCGCG AGCGCGGTTT-3' (SEQ ID NO:13) (forward) and 5'-CGCTGCGCCCAGATGTT-3' (SEQ ID NO:14) (reverse), corresponding to the SOCS-3 promoter region sequences -1005 to -983 and -754 to -737, respectively. Sequences of the unmethylation-specific primers were: 5'-TGTGGTGGTTGTTTATATATTTGTGAGTGTGGTT-3' (SEQ ID NO:15) (forward) and 5'-CAACCAACAATAACCCACACTACACCCA-3'(SEQ ID NO:16) (reverse), corresponding to the SOCS-3 promoter region sequences -1018 to -984 and -748 to -720, respectively.

Transient Transfection and Colony Formation Assay

For transient transfection experiments, cells ($2\times10^5$) were plated in six-well plates 24 hrs before transfection. Lipofectamine 2000 (Life Technologies) was used to mediate transfection using 5.0 mg of SOCS-3 cDNA construct in pcDNA3 vector or 5.0 mg empty pcDNA3 vector as control, according to the manufacture's protocol. Transfected cells were striped and plated on 10 cm cell culture dishes at 48 hours after transfection. The cells were then selected by G418 (400 mg/ml.). Colonies were stained by using 0.5% Methylene Blue and counted 4 weeks after the transfection.

Apoptosis Analysis

One week after transfection (as described above), the cells were harvested by trypsinization and stained using an Annexin V FITC Apoptosis Detection Kit (Oncogene, Cambridge, Mass.), according to the manufacturer's protocol. Then stained cells were immediately analyzed by flow cytometry (FACScan; Decton Dickinson, Franklin Lake, N.J.). Early apoptotic cells with exposed phosphatidylserine but intact cell membranes bound to Annexin V-FITC but excluded propidium iodide. Cells in necrotic or late apoptotic stages were labeled with both Annexin V-FITC and propidium iodide.

Statistical Analysis

Data shown represent mean values (+S.D.). Student T-Test was used for comparing activities of different constructs and treatments.

Example 1

Correlation of Promoter Hypermethylation with Silencing of SOCS-3 in Cell Lines

Figure 1B:
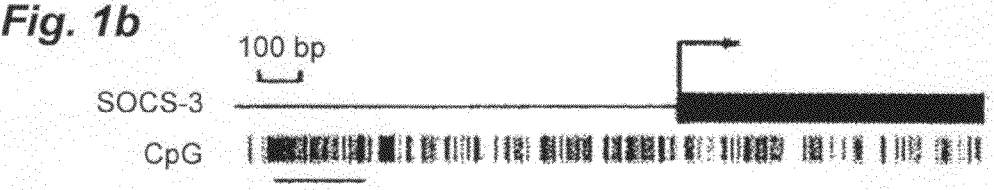
Figure 1C:
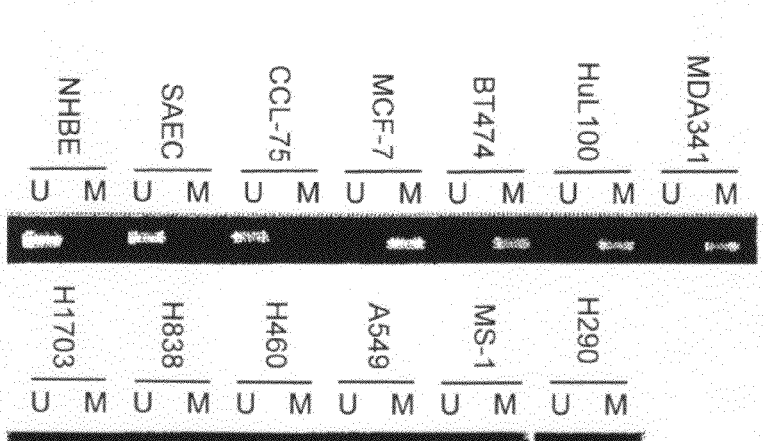

SOCS-3 expression was exampled in various cell lines. The results (FIG. 1a) show that the SOCS-3 transcript was missing or dramatically under-expressed in three of four non-small-cell lung cancer (NSCLC) cell lines, one of two mesothelioma cell lines, and all four breast cancer cell lines tested. In contrast, SOCS-3 expression was detectable in all three normal controls. To identify an underlying mechanism for loss of SOCS-3 expression in cancer cells, the methylation status of CpG islands in the SOCS-3 promoter region in these cell lines was analyzed (FIG. 1b). All cancer cell lines tested (NCIH1703, NCI-H460, NCI—H838, NCI-H290, MCF-7, BT474, HuL100 and MDA341) that lacked SOCS-3 expression were hyper-methylated using methylation-specific PCR (MSP) (FIG. 1c). In contrast, no hyper-methylation was observed in the three normal controls that expressed SOCS-3 (FIG. 1c).

Figure 2:
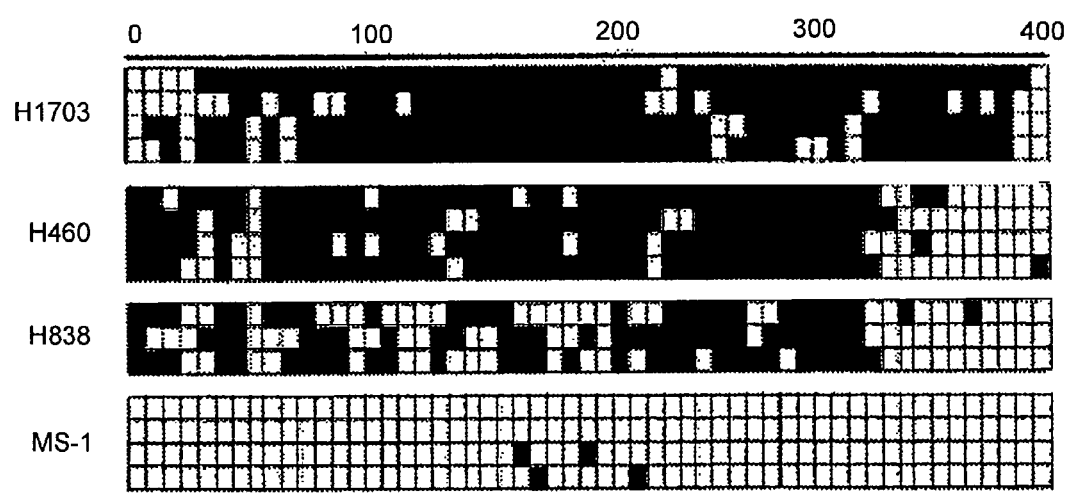
FIG. 2 shows exemplary results of bisulfite-sequencing analysis of NSCLC and mesothelioma cell lines. Open and filled squares represent unmethylated and methylated CpG islands, respectively. Four clones of PCR products amplified from bisulfite treated genomic DNA for each cell line were sequences.

Bisulfite sequencing was also used to evaluate the methylation status of 55 CpG sites in the 413 by of the SOCS-3 promoter region in several cell lines. This region contains both functional STAT-binding sites and a TATA box that are highly conserved in both mouse and rat SOCS-3 promoters, and can function as a minimal promoter (19). Consistent with MSP results, these CpG islands in all three NSCLC cell lines tested were densely methylated. The mesothelioma cell line, MS-1, expresses SOCS-3, showed no dense methylation in these CpG islands (FIG. 2). These results indicate that SOCS-3 expression in NSCLC, breast cancer and mesothelioma cell lines correlates with dense methylation of the functional and conserved SOCS-3 promoter region.

Example 2

Figure 3A:
FIG. 3 provides exemplary data showing the correlation of methylation in the SOCS-3 promoter region with silencing of the SOCS-3 gene in primary non-small cell lung carcinoma (NSCLC) tissue samples. Panel a is a Northern blot of eight matched pairs of normal and lung cancer tissue probed with SOCS-3 cDNA. A specific probe of L19 ribosomal protein was used as a standard. Panel b is MSP analysis of eight matched pairs of normal (N) and lung cancer (T) tissue. Bands in lanes "U" and "M" are as indicated in FIG. 1c.
Figure 3B:
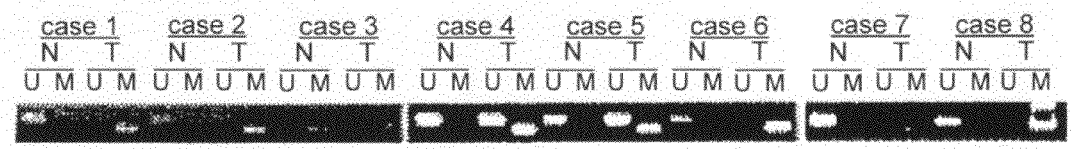

Correlation of Promoter Hypermethylation with Silencing of SOCS-3 in Primary NSCLC Tissue Samples SOCS-3 expression and methylation status in the SOCS-3 promoter region was examined in primary NSCLC tissue samples. Among eight matched pairs of surgically resected early stage lung cancers, seven cancer samples (87.5%) had no or less SOCS-3 mRNA than their matched normal counterpart (FIG. 3a). Consistent with the lack or diminished SOCS-3 expression, we observed aberrant methylation in all seven tumor samples, but not in their matched normal samples by MSP (FIG. 3b). In case 3, methylation was observed in both the cancer and the matched normal sample. The methylation observed in normal tissue may be due to unavoidable contamination of cancer cells in the non-cancer specimen or pre-malignant changes of peri-tumoral normal tissue. Partial methylation observed in the tumor samples can also be interpreted as unavoidable contamination of normal cells in the cancer specimens. These data indicate that silencing of SOCS-3 is correlated with hyper-methylation of CpG islands in its promoter in primary NSCLC tissue samples.

Figure 4A:
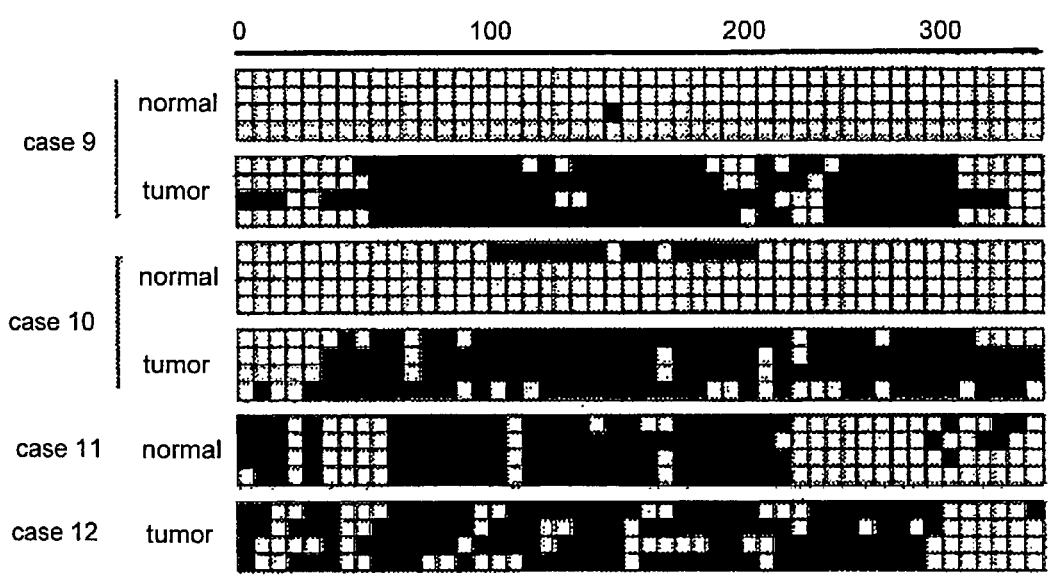
FIG. 4 provides exemplary data showing methylation analysis of additional NSCLC primary tissue samples. Panel a shows bisulfite-sequencing examples of the SOCS-3 promoter region in NSCLC primary tissue samples. Open and filled squares represent unmethylated and methylated CpG islands, respectively. Four clones of PCR products amplified from bisulfite treated genomic DNA were sequence for each sample. The region analyzed is as indicated in FIG. 1b. Panel b is summary of methylation status of the SOCS-3 promoter region in 18 NSCLC primary tissue samples. Gene name is indicated on the left and case numbers are indicated at the top. Each gray (methylation) or open (no methylation) square represents a primary tumor.
Figure 4B:
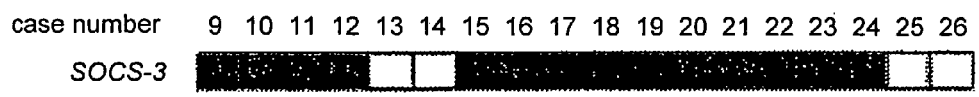

We also examined methylation of CpG islands in the SOCS-3 promoter in 18 additional surgically resected NSCLC primary tissue samples by either bisulfite sequencing or MSP. Of the 18 tumor samples, 2 had matched normal tissue. Six tissue samples, including the two matched pairs, were selected for bisulfite sequencing. Dense methylation was detected in those CpG sites in 4 f the 5 tumor samples, including both tumor samples of the two matched pairs. In contrast, only one of four clones sequenced from one paired normal sample demonstrated minimal regional methylation (FIG. 4a). MSP analysis also detected methylation in 10 of the remaining 12 tumor samples (data not shown). In summary, methylation in the SOCS-3 promoter region was detected in 14 of the18 (77.8%) NSCLC primary cancer tissue samples that we examined (FIG. 4b).

Example 3

Restoration of SOCS-3 Causes Cell Growth Suppression

We investigated whether restoration of SOCS-3 would result in growth suppression in the lung cancer cell lines where SOCS-3 was silenced by promoter hypermethylation. One week after transfection and subsequent drug selection, significant decreases in live cell numbers in H460 cells transfected with SOCS-3 (approximately 24% cells are alive) were observed compared to the empty vector-transfected control transfectants (approximately 86% cells are alive) (P<0.005) (FIGS. 5a, b and c). Flow cytometry analysis showed a significantly higher level of apoptosis induction in SOCS-3- transfected H460 cells than empty vector-transfected H460 cells (approximately 41% and 9% at one week after transfection, respectively) (P<0.005) (FIG. 5d). These results indicate that restoration of the SOCS-3 expression induces apoptosis and suppresses cell growth.

Figure 5E:
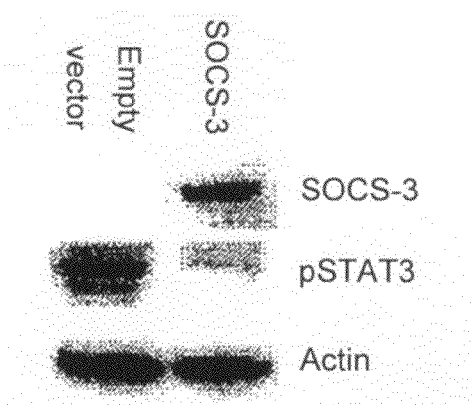
FIG. 5 provides exemplary data showing growth suppression in NSCLC cells by restoration of the SOCS-3 gene. Panels a and b show morphology of H460 cells (SOCS-3 methylation-silenced) after transfection of empty vector or SOCS-3 expression vector, and subsequent selection with G418 for one week, respectively. Panel c shows percentage of live H460 cells after transfection of empty vector or SOCS-3 expression vector, and subsequent selection with G418 for one week. Results are means with error bars (S.D.). Panel d is an example of apoptotic analysis using flow cytometry on H460 cells one week after transfection of empty vector or SOCS-3 expression vector. FL1-H represents Annexin V-FITC staining. Panel e is a Western analysis of endogenous phosphorylated STAT3 (active form) and SOCS-3 proteins in H460 cells after transfection of empty vector or SOCS-3 expression vector. β-actin was used as loading control. Whole cell extracts were prepared after transfection and selection with G418 for four weeks. Panel f shows colony formation assay using H460 cells. The cells were transfected with empty vector or SOCS-3 expression vector, and selection with G418 for four week. The bar graph shows the average of colony numbers in triplicated experiments. Error bars are standard deviations (S.D.).
Figure 5F:
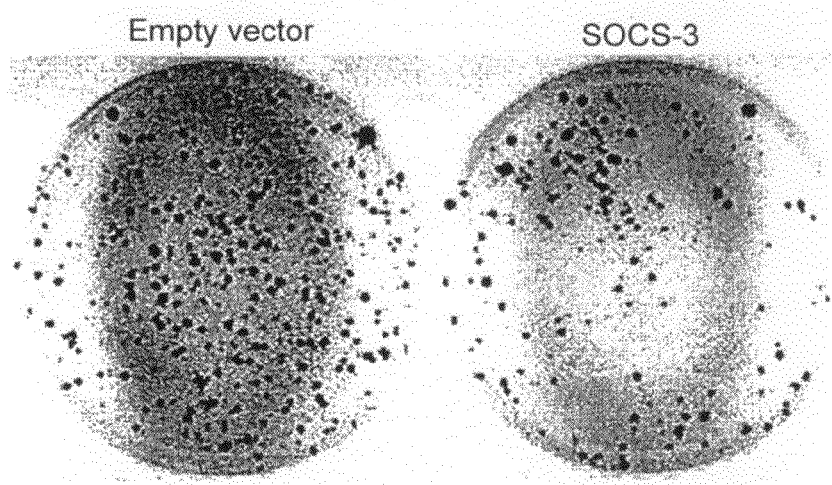
Figure 5F:
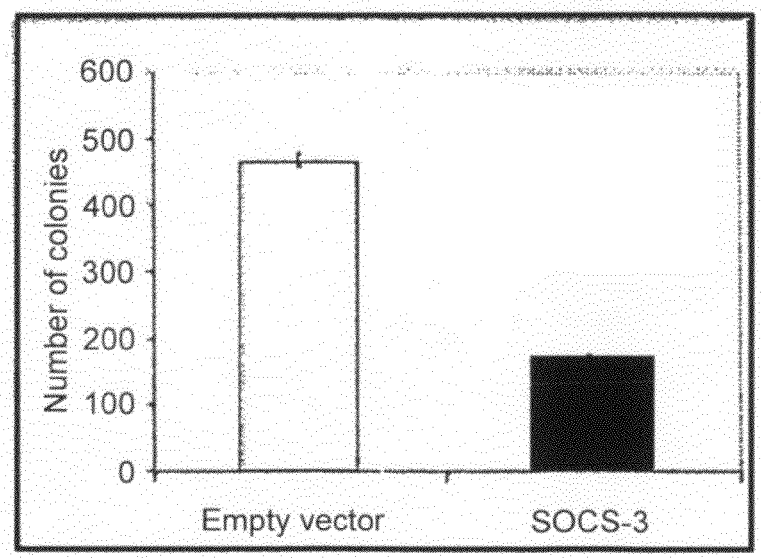
Figure 6:
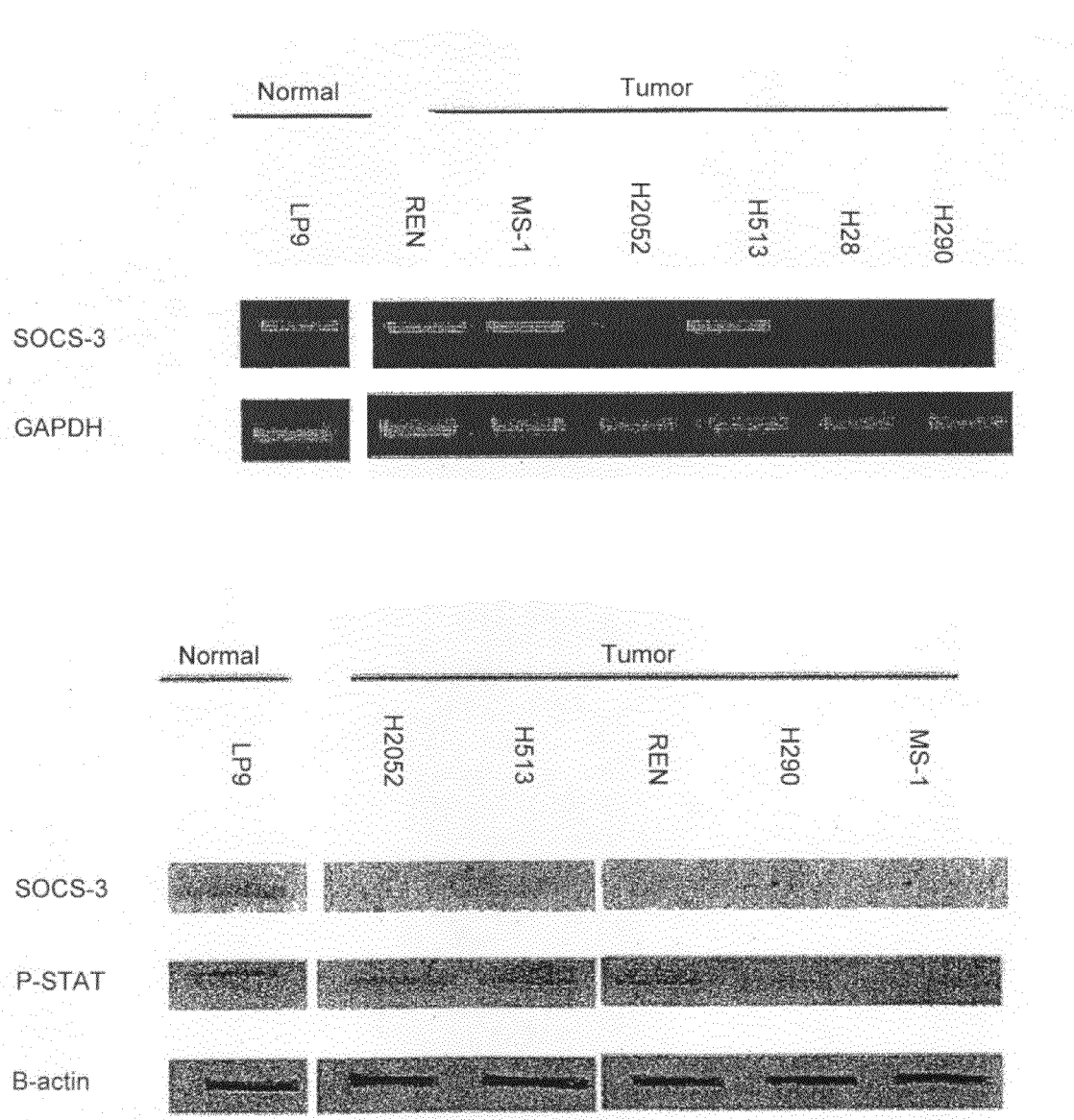
FIG. 6 provides exemplary data showing SOCS-3 and pSTAT3 expression in mesothelioma primary tissue and cell lines. Upper panel shows the results of an RNA analysis. RNA was extracted from a normal mesothelioma cell line (LP9) and from several malignant mesothelioma cell lines. After extraction, RNA was subjected to reverse transcriptase PCR(RT-PCR). The catalytic enzyme GAPDH was used as a positive control to test for RNA quality and loading. The lower panel depicts a western blot analysis of expression of SOCS-3 protein in 6 cell lines along with the corresponding P-STAT expression levels. Commercial SOCS-3 and P-STAT3 antibodies were used with B-actin served as a loading control.
Figure 8:
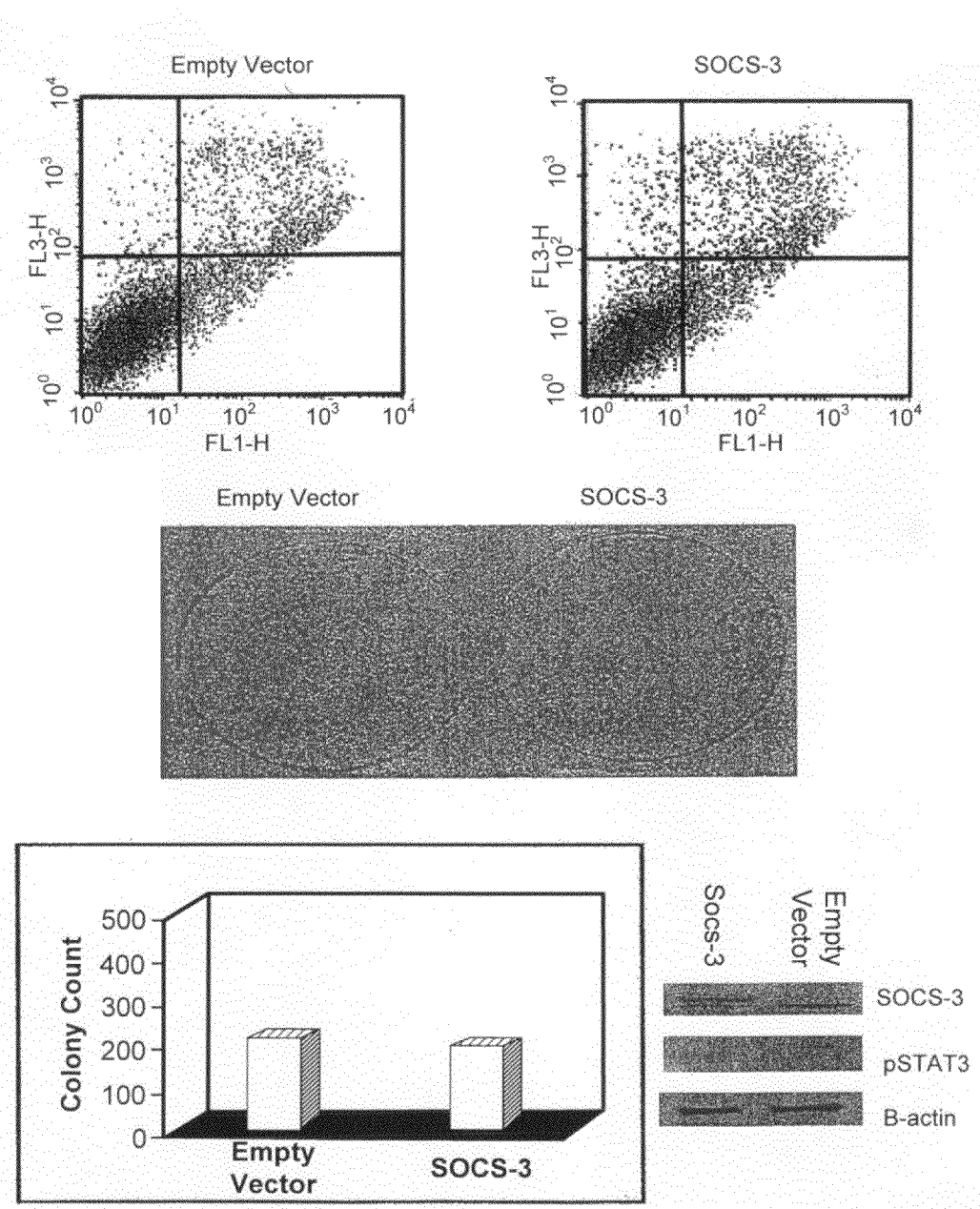
FIG. 8 provides exemplary data showing transfection of SOCS-3 in MS-1, a cell line lacking methylation in the SOCS-3 promoter. The upper panels show the results of flow cytometry performed on SOCS-3-transected and empty-vector-transfected cells. The incidence of apoptosis for the empty vector control is 10.8% compared to 11.1% for the SOCS-3 transfected cells. The additional panels display a colony count assay with the values of the count depicted in the graph to the side. Expression data showing SOCS-3 and P-STAT3 levels in transfected cells is provided in the bottom panel.
Figure 9:
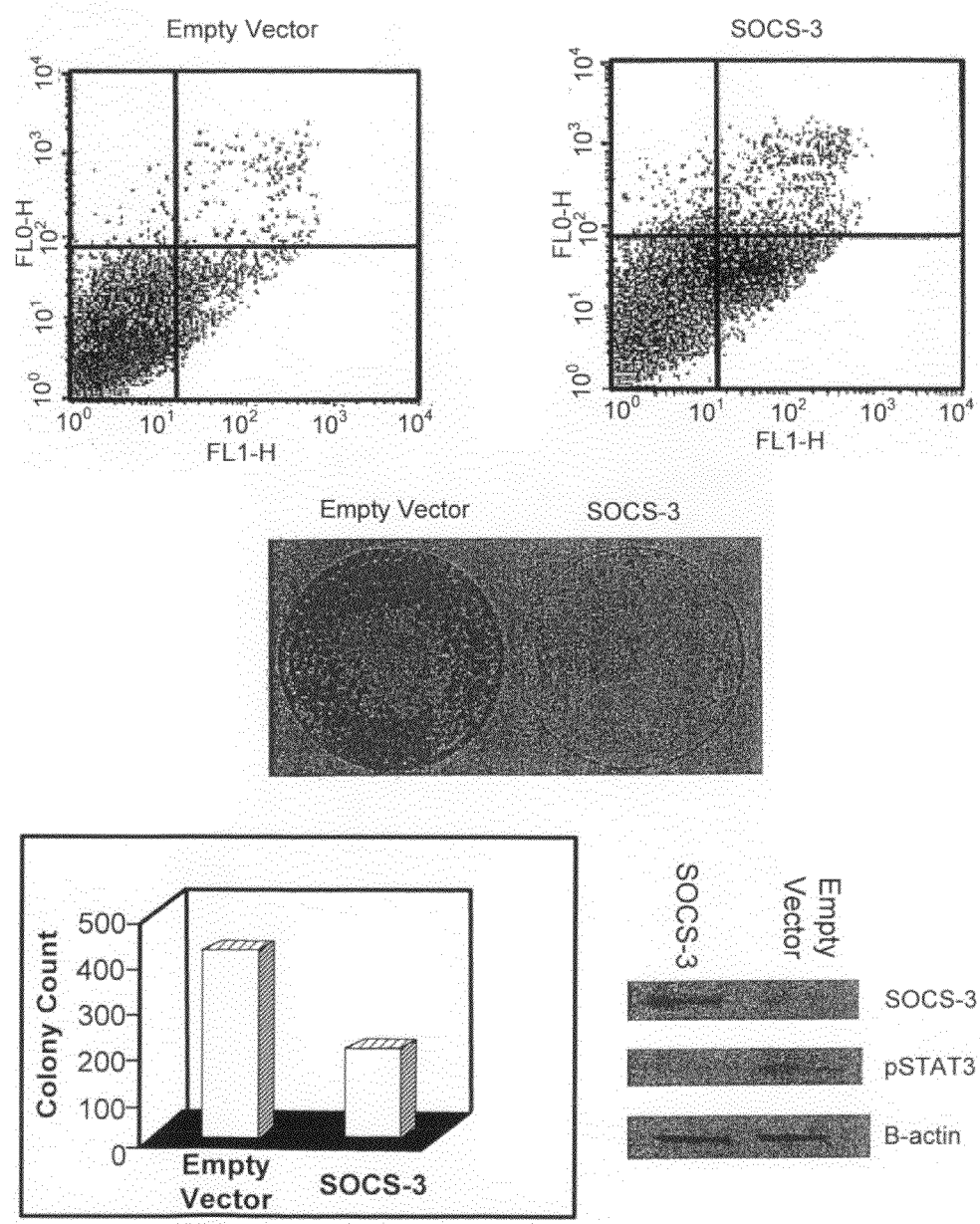
FIG. 9 provides exemplary data showing transfection of SOCS-3 in H28, a cell line with a methylated SOCS-3 promoter. The upper panels show the results of flow cytometry performed on SOCS-3-transected and empty-vector-transfected cells. The incidence of apoptosis for the empty vector control is 13.3% compared to 43% for the SOCS-3 transfected cells. The additional panels display a colony count assay with the values of the count depicted in the graph to the side. Expression data showing SOCS-3 and P-STAT3 levels in transfected cells is provided in the bottom panel.

Also of note was the observation that restoration of SOCS-3 decreased the level of constitutive STAT3 phosphorylation in the H460 cells tested (FIG. 5e). In addition, after selection of drug-resistant colonies for four weeks, the colony numbers of SOCS-3 transfected cells decreased compared to that of empty vector-transfected cells (P<0.005) (FIG. 5f).

Example 4

SOCS-3 in Mesothelioma

SOCS-3 expression and methylation were analyzed in various mesothelioma tumors and cell lines. The results are shown in FIGS. 5-9. The analyses show that SOC-3 is under expressed in mesothelioma and that the SOCS-3 promoter is hypermethylated.

The above examples are provided by way of illustration only and not by way of limitation. Those of skill in the art will readily recognize a variety of noncritical parameters that could be changed or modified to yield essentially similar results.

All publications, patent applications, accession numbers, and other references cited in this specification are herein incorporated by reference as if each individual publication, patent application, accession number or other reference was specifically and individually indicated to be incorporated by reference.

SEQ ID NO:1 Human SOCS-3 Nucleic Acid Sequence cds: 107 ... 784

```
GCGCCTTCCTCTCCGCAGCCCCCGGGATGCGGTAGCGGCCGCTGTG

CGGAGGCCGCGAAGCAGCTGCAGCCGCCGCCGCGCAGATCCACGCTG

GCTCCGTGCGCCATGGTCACCCACAGCAAGTTTCCCGCCGCCGGGAT

GAGCCGCCCCTGGACACCAGCCTGCGCCTCAAGACCTTCAGCTCCA

AGAGCGAGTACCAGCTGGTGGTGAACGCAGTGCGCAAGCTGCAGGAG

AGCGGCTTCTACTGGAGCGCAGTGACCGGCGGCGAGGCGAACCTGCT

GCTCAGTGCCGAGCCCGCCGGCACCTTTCTGATCCGCGACAGCTCGG

ACCAGCGCCACTTCTTCACGCTCAGCGTCAAGACCCAGTCTGGGACC

AAGAACCTGCGCATCCAGTGTGAGGGGGGCAGCTTCTCTCTGCAGAG

CGATCCCCGGAGCACGCAGCCCGTGCCCCGCTTCGACTGCGTGCTCA

AGCTGGTGTACCACTACATGCCGCCCCCTGGAGCCCCCTCCTTCCCC

TCGCCACCTACTGAACCCTCCTCCGAGGTGCCCGAGCAGCCGTCTGC

CCAGCCACTCCCTGGGAGTCCCCCCAGAAGAGCCTATTACATCTACT

CCGGGGGCGAGAAGATCCCCCTGGTGTTGAGCCGGCCCCTCTCCTCC

AACGTGGCCACTCTTCAGCATCTCTGTCGGAAGACCGTCAACGGCCA

CCTGGACTCCTATGAGAAAGTCACCCAGCTGCCGGGGCCCATTCGGG

AGTTCCTGGACCAGTACGATGCCCCGCTTTAAGGGGTAAAGGGCGCA

AAGGGCATGGGTCGGGAGAGGGGACGCAGGC CCCTCTCCTCCGTGG

CACAT
```

SEQ ID NO:2 Human SOCS-3 Polypeptide Sequence

```
MVTHSKFPAAGMSRPLDTSLRLKTFSSKSEYQLVVNAVRKLQESGFY

WSAVTGGEANLLLSAEPAGTFLIRDSSDQRHFFTLSVKTQSGTKNLR

IQCEGGSFSLQSDPRSTQPVPRFDCVLKLVYHYMPPPGAPSFPSPPT

EPSSEVPEQPSAQPLPGSPPRRAYYTYSGGEKIPLVLSRPLSSNVAT

LQ HLCRKTVNGH LDSYEKVTQLPGPIREFLDQYDAPL
```

SEQ ID NO:3 Human SOCS-3 Promoter Sequence

The first position in the sequence is –1084. Position +1 is at the "A" of the ATG start methionine, which is designated with an open box. The shadowed boxes indicate STAT-binding sites. The bolded region is termed a "G-rich region", and the underlined region is the TATA box.

GTGCAGAGTA GTGACTAAAC ATTACAAGAA GACCGGCCGG GCAGTTCCAGGAA TCGGGGG

GCGGGGCGCG GCGGCCGCCTATATACCCGC GAGCGCGGCC TCCGCGGCGG CTCCGACTTG

GACTCCCTGC TCCGCTGCTG CCGCTTCGGC CCCGCACGCA GCCAGCCGCC CGCCGCCCGC

CCGGCCCAGC TCCCGCCGCG GCCCCTTGCC GCGGTCCCTC TCCTGGTCCC CTCCCGGTTG

GTCCGGGGGT GCGCAGGGGG CAGGGCGGGC GCCCAGGGGA AGCTCGAGGG ACGCGCGCGC

GAAGGCTCCT TTGTGGACTT CACGGCCGCC AACATCTGGG CGCAGCGCGG GCCACCGCTG

GCCGTCTCGC CGCCGCGTCG CCTTGGGGAC CCGAGGGGGC TCAGCCCCAA GGACGGAGAC

TTCGATTCGG GACCAGGTAG GAAGGAGGAG CGCGGCGTGG GGAGGGGTCT CGCTCAGTCC

CGGGAGCTTT TCCCGGTTTC CCCTCCCCTT CCCGGGTCAT TCCCGGCAGG GAGGTGACGA

GGTAGGGGCA GAGCGGATGG AAGCCGGAGA TCCCAGGTTC CCGGAATACT CCGGCTGGGG

CCTTCGGGCT TCTCCTGTCC CCTCCCTACC CCCGTGCCTC GGGTTTCTCC CTCCGTCCAC

ACCGCCCGGG GCTACTGGAC TGAGCGGCgc ccaggcagtc ccggggccct tctcctgtcc caacccggca cactcctgag acctaacttc cgcgcgcgag tttcccacgc tgcgccttg cagtgcgcgc ctgggaaggg gctgcccggg gccaccctgc cggcagggcg ggagccgtgc gggctccgtg aggcgcctgg atcggagcgc gggcccagga gagggccccc ggggcagtgg gtgccccagt cgctcggcga aggcagggga gccggggcgg gccgggcgcg ctggagggtt ccgggcactc aacgcgctcg cgccttcctc tccgcagccc ccgggatgc ggtagcggcc gctgtgcgga ggccgcgaag gcgcc atg

---

What is claimed is:

1. A method of detecting lung cancer, breast cancer, or mesothelioma in a patient, the method comprising:
   determining the amount of methylation of the CpG residues occurring within the region from −1005 to −983 or from −754 to −737 of a SOCS-3 promoter comprising SEQ ID NO: 3 in a biological sample from the patient, wherein said biological sample is a sample of lung tissue, breast tissue or mesothelium; and
   determining that lung cancer, breast cancer, or mesothelioma is present in the patient when the amount of methylation of the SOCS-3 promoter in the biological sample is elevated relative to the amount of methylation of the SOCS-3 promoter in a sample of normal lung tissue, breast tissue or mesothelium, respectively,
   thereby detecting the presence of lung cancer, breast cancer, or mesothelioma in the patient.

2. The method of claim 1, wherein the amount of methylation of the SOCS-3 promoter is determined using bisulfite sequencing.

3. The method of claim 1, wherein the amount of methylation of the SOCS-3 promoter is determined using methylation-specific PCR.

4. The method of claim 1, wherein the amount of methylation is detected using a methylation-sensitive restriction enzyme.

* * * * *

UNITED STATES PATENT AND TRADEMARK OFFICE
CERTIFICATE OF CORRECTION

PATENT NO. : 8,450,062 B2
APPLICATION NO. : 12/701432
DATED : May 28, 2013
INVENTOR(S) : Biao He et al.

It is certified that error appears in the above-identified patent and that said Letters Patent is hereby corrected as shown below:

In the Specification

Column 1, line 24, replace the word "MK" with --JAK--

Column 3, line 2, replace the word "of" with --of:--

Column 3, line 49, replace the word "by" with --bp--

Column 9, lines 14-15, replace the word "carboxyglutamate" with --γ-carboxyglutamate--

Column 9, line 17, replace the word "a" with --α--

Column 11, line 4, replace the word "Eghoim" with --Egholm--

Column 11, line 18, replace the word "Jeff's" with --Jeffs--

Column 17, lines 23-24, replace the word "phosphoraraidite" with --phosphoramidite--

Column 17, line 61, replace the word "by" with --bp--

Column 21, line 57, replace the word "Kwok" with --Kwoh--

Column 24, line 21, delete the word "10,"

Column 30, line 13, replace the word "Feigner" with --Felgner--

Column 30, line 29, replace the word "Transfectarm™" with --Transfectam™--

Column 30, line 32, replace the word "Feigner" with --Felgner--

Signed and Sealed this
First Day of April, 2014

Michelle K. Lee
*Deputy Director of the United States Patent and Trademark Office*

CERTIFICATE OF CORRECTION (continued)
U.S. Pat. No. 8,450,062 B2

Column 35, line 30, replace the word "by" with --bp--

Column 35, line 33, replace the word "by" with --bp--

Column 36, line 55, replace the word "by" with --bp--

Column 38, line 58, replace the sequence
"EPSSEVPEQPSAQPLPGSPPRRAYYTYSGGEKIPLVLSRPLSSNVAT" with
--EPSSEVPEQPSAQPLPGSPPRRAYYIYSGGEKIPLVLSRPLSSNVAT--

Column 39, replace last line of sequence before the SEQUENCE LISTING
"gctgtgcgga ggccgcgaag gcgccatg" with
-- gctgtgcgga ggccgcgaag cagctgcagc cgccgccgcg cagatccacg ctggctccgt gcgccatg --

SEQUENCE LISTING

<160> NUMBER OF SEQ ID NOS: 16

<210> SEQ ID NO 1
<211> LENGTH: 850
<212> TYPE: DNA
<213> ORGANISM: Homo sapiens
<220> FEATURE:
<223> OTHER INFORMATION: suppressor of cytokine signaling 3 (SOCS-3),
      cytokine-induced SH2 protein 3 (CIS-3, Cish3),
      STAT-induced STAT inhibitor 3 (SSI-3, SSI3),
      atopic dermatitis 4 (ATOD4), MGC71791

<400> SEQUENCE: 1
gcgccttcct ctccgcagcc ccccgggatg cggtagcggc cgctgtgcgg aggccgcgaa    60
gcagctgcag ccgccgccgc gcagatccac gctggctccg tgcgccatgg tcacccacag   120
caagtttccc gccgccggga tgagccgccc cctggacacc agcctgcgcc tcaagacctt   180
cagctccaag agcgagtacc agctggtggt gaacgcagtg cgcaagctgc aggagagcgg   240
cttctactgg agcgcagtga ccggcggcga ggcgaacctg ctgctcagtg ccgagcccgc   300
cggcaccttt ctgatccgcg acagctcgga ccagcgccac ttcttcacgc tcagcgtcaa   360
gacccagtct gggaccaaga acctgcgcat ccagtgtgag ggggcagct tctctctgca   420 gagcgatccc cggagcacgc agcccgtgcc ccgcttcgac tgcgtgctca agctggtgta   480
ccactacatg ccgccccctg gagccccctc cttcccctcg ccacctactg aaccctcctc   540
cgaggtgccc gagcagccgt ctgccagcc actccctggg agtcccccca agagcta    600 ttacatctac tccggggcg agaagatccc cctggtgttg agccggccc tctcctccaa    660 cgtggccact cttcagcatc tctgtcggaa gaccgtcaac ggccacctgg actcctatga   720

-continued

| | | | |
|---|---|---|---|
| gaaagtcacc cagctgccgg ggcccattcg ggagttcctg gaccagtacg atgccccgct | | | 780 |
| ttaagggta aagggcgcaa agggcatggg tcgggagagg ggacgcaggc ccctctcctc | | | 840 |
| cgtggcacat | | | 850 |

<210> SEQ ID NO 2
<211> LENGTH: 225
<212> TYPE: PRT
<213> ORGANISM: Homo sapiens
<220> FEATURE:
<223> OTHER INFORMATION: suppressor of cytokine signaling 3 (SOCS-3),
    cytokine-induced SH2 protein 3 (CIS-3, Cish3),
    STAT-induced STAT inhibitor 3 (SSI-3, SSI3),
    atopic dermatitis 4 (ATOD4)

<400> SEQUENCE: 2

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His Tyr Met
        115                 120                 125

Pro Pro Pro Gly Ala Pro Ser Phe Pro Ser Pro Thr Glu Pro Ser
    130                 135                 140

Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225

<210> SEQ ID NO 3
<211> LENGTH: 1088
<212> TYPE: DNA
<213> ORGANISM: Homo sapiens
<220> FEATURE:
<221> NAME/KEY: promoter
<222> LOCATION: (1)...(1088)
<223> OTHER INFORMATION: suppressor of cytokine signaling 3 (SOCS-3),
    cytokine-induced SH2 protein 3 (CIS-3, Cish3),
    STAT-induced STAT inhibitor 3 (SSI-3, SSI3),
    atopic dermatitis 4 (ATOD4) promoter

<400> SEQUENCE: 3

| | | | |
|---|---|---|---|
| gtgcagagta gtgactaaac attacaagaa gaccggccgg gcagttccag gaatcggggg | | | 60 |

-continued

```
gcggggcgcg cggccgcct atatacccgc gagcgcggcc tccgcggcgg ctccgacttg    120
gactccctgc tccgctgctg ccgcttcggc cccgcacgca gccagccgcc cgccgcccgc    180
ccggcccagc tcccgccgcg gcccccttgcc gcggtccctc tcctggtccc ctccggttg    240 gtccgggggt gcgcagggg cagggcgggc ccccagggga agctcgaggg acgcgcgcgc    300
gaaggctcct ttgtggactt cacggccgcc aacatctggg cgcagcgcgg gccaccgctg    360
gccgtctcgc cgccgcgtcg ccttggggac ccgaggggc tcagccccaa ggacggagac    420
ttcgattcgg gaccaggtag gaaggaggag cgcggcgtgg ggagggtct cgctcagtcc    480 cgggagcttt tcccggtttc ccctccctt cccgggtcat tccggcagg gaggtgacga    540 ggtaggggca gagcggatgg aagccggaga tcccaggttc ccggaatact ccggctgggg    600
ccttcgggct tctcctgtcc cctccctacc cccgtgcctc gggtttctcc ctccgtccac    660
accgccgggg gctactggac tgagcggcgc ccaggcagtc ccggggccct tctcctgtcc    720
caacccggca cactcctgag acctaacttc cgcgcgcgag tttcccacgc tgcgcccttg    780
cagtgcgcgc ctgggaaggg gctgcccggg gccaccctgc cggcagggcg ggagccgtgc    840
gggctccgtg aggcgcctgg atcgagcgc gggccccagga gagggcccccc ggggcagtgg    900 gtgccccagt cgctcggcga aggcagggga gccggggcgg gccgggcgcg ctggagggtt    960
ccgggcactc aacgcgctcg cgccttcctc tccgcagccc cccgggatgc ggtagcggcc    1020
gctgtgcgga ggccgcgaag cagctgcagc cgccgccgcg cagatccacg ctggctccgt    1080
gcgccatg                                                            1088
```

<210> SEQ ID NO 4
<211> LENGTH: 200
<212> TYPE: PRT
<213> ORGANISM: Artificial Sequence
<220> FEATURE:
<223> OTHER INFORMATION: synthetic poly-Gly flexible linker
<220> FEATURE:
<221> NAME/KEY: VARIANT
<222> LOCATION: (6)...(200)
<223> OTHER INFORMATION: Xaa = Gly or absent

<400> SEQUENCE: 4

```
Gly Gly Gly Gly Gly Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa
145                 150                 155                 160
```

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa
        195                 200

<210> SEQ ID NO 5
<211> LENGTH: 22
<212> TYPE: DNA
<213> ORGANISM: Artificial Sequence
<220> FEATURE:
<223> OTHER INFORMATION: synthetic methylation-specific forward primer

<400> SEQUENCE: 5
tatatattcg cgagcgcggt tt                                          22

<210> SEQ ID NO 6
<211> LENGTH: 17
<212> TYPE: DNA
<213> ORGANISM: Artificial Sequence
<220> FEATURE:
<223> OTHER INFORMATION: synthetic methylation-specific reverse primer

<400> SEQUENCE: 6
cgctgcgccc agatgtt                                                17

<210> SEQ ID NO 7
<211> LENGTH: 34
<212> TYPE: DNA
<213> ORGANISM: Artificial Sequence
<220> FEATURE:
<223> OTHER INFORMATION: synthetic unmethylation-specific forward primer

<400> SEQUENCE: 7
tgtggtggtt gtttatatat ttgtgagtgt ggtt                             34

<210> SEQ ID NO 8
<211> LENGTH: 28
<212> TYPE: DNA
<213> ORGANISM: Artificial Sequence
<220> FEATURE:
<223> OTHER INFORMATION: synthetic unmethylation-specific reverse primer

<400> SEQUENCE: 8
caaccaacaa taacccacac tacaccca                                    28

<210> SEQ ID NO 9
<211> LENGTH: 20
<212> TYPE: DNA
<213> ORGANISM: Artificial Sequence
<220> FEATURE:
<223> OTHER INFORMATION: synthetic RT-PCR forward primer for 579 bp
      fragment of SOCS-3 cDNA

<400> SEQUENCE: 9
gtcacccaca gcaagtttcc                                             20

<210> SEQ ID NO 10
<211> LENGTH: 20
<212> TYPE: DNA
<213> ORGANISM: Artificial Sequence
<220> FEATURE:
<223> OTHER INFORMATION: synthetic RT-PCR reverse primer for 579 bp
      fragment of SOCS-3 cDNA -continued

<400> SEQUENCE: 10
ccgacagaga tgctgaagag                                          20

<210> SEQ ID NO 11
<211> LENGTH: 21
<212> TYPE: DNA
<213> ORGANISM: Artificial Sequence
<220> FEATURE:
<223> OTHER INFORMATION: synthetic forward primer to amplify SOCS-3
      promoter region of bisulfite-modified genomic DNA

<400> SEQUENCE: 11
gtgtagagta gtgattaaat a                                        21

<210> SEQ ID NO 12
<211> LENGTH: 21
<212> TYPE: DNA
<213> ORGANISM: Artificial Sequence
<220> FEATURE:
<223> OTHER INFORMATION: synthetic reverse primer to amplify SOCS-3
      promoter region of bisulfite-modified genomic DNA

<400> SEQUENCE: 12
tccttaaaac taaaccccct c                                        21

<210> SEQ ID NO 13
<211> LENGTH: 22
<212> TYPE: DNA
<213> ORGANISM: Artificial Sequence
<220> FEATURE:
<223> OTHER INFORMATION: synthetic methylation-specific forward primer
      to amplify SOCS-3 promoter region of
      bisulfite-modified genomic DNA

<400> SEQUENCE: 13
tatatattcg cgagcgcggt tt                                       22

<210> SEQ ID NO 14
<211> LENGTH: 17
<212> TYPE: DNA
<213> ORGANISM: Artificial Sequence
<220> FEATURE:
<223> OTHER INFORMATION: synthetic methylation-specific reverse primer
      to amplify SOCS-3 promoter region of
      bisulfite-modified genomic DNA

<400> SEQUENCE: 14
cgctgcgccc agatgtt                                             17

<210> SEQ ID NO 15
<211> LENGTH: 25
<212> TYPE: DNA
<213> ORGANISM: Artificial Sequence
<220> FEATURE:
<223> OTHER INFORMATION: synthetic unmethylation-specific forward primer
      to amplify SOCS-3 promoter region of
      bisulfite-modified genomic DNA

<400> SEQUENCE: 15
tgtttatata tttgtgagtg tggtt                                    25

<210> SEQ ID NO 16
<211> LENGTH: 28
<212> TYPE: DNA
<213> ORGANISM: Artificial Sequence
<220> FEATURE:
<223> OTHER INFORMATION: synthetic unmethylation-specific reverse primer
      to amplify SOCS-3 promoter region of

```
bisulfite-modified genomic DNA

<400> SEQUENCE: 16
caaccaacaa taacccacac tacaccca                                              28
```